(12) United States Patent
Hidai et al.

(10) Patent No.: US 6,723,807 B2
(45) Date of Patent: Apr. 20, 2004

(54) CATALYST COMPONENT AND CATALYST FOR ADDITION POLYMERIZATION, AND PROCESS FOR PRODUCING ADDITION POLYMER

(75) Inventors: Masanobu Hidai, Tokyo (JP); Masaaki Nabika, Chiba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/324,122

(22) Filed: Dec. 20, 2002

(65) Prior Publication Data

US 2003/0158355 A1 Aug. 21, 2003

Related U.S. Application Data

(63) Continuation-in-part of application No. 09/986,472, filed on Nov. 8, 2001, now abandoned.

(30) Foreign Application Priority Data

Nov. 13, 2000 (JP) .......................... 2000-344977

(51) Int. Cl.$^7$ ................................. C08F 4/68
(52) U.S. Cl. .................... 526/116; 526/115; 526/117; 526/170; 526/171; 526/172; 526/164; 526/134; 526/169; 526/169.1; 526/169.2; 502/103; 556/28; 556/51; 556/52; 556/57
(58) Field of Search .................. 526/116, 115, 526/117, 170, 171, 172, 161, 134, 169, 169.1, 169.2; 502/103; 556/51, 52, 28, 57

(56) References Cited

FOREIGN PATENT DOCUMENTS

| GB | 1259856 | 1/1972 |
|---|---|---|
| WO | 9640805 | 10/1996 |

OTHER PUBLICATIONS

Mizobe, Y.; Yokobayashi, Y.; Oshita, H.; Takahashi, T.; Hidai, M. Organometallics 1994, 13, 3764–3766.*

Green, Malcolm L. H. et al: μ–Dinitrogen–bis{[1,2–bis-(dimethylphosphino)ethane]hydrido–[η–(1,3,5–trimethylbenzene)]molybdenum} Cation; pp. 2164–2166.

Konstantinos D. Demadis et al: Localization in trans,trans–[(tpy)(Cl)$_2$Os$^{II}$(N$_2$)Os$^{II}$(Cl)$_2$(tpy)]$^+$ (tpy =2,2':6',2"–Terpyridine);Inorganic Chemistry, vol. 36, No. 25, 1997; pp. 5678–5679.

Leslie D. Field et al: Synthesis and Properties of Iron(II) Hydride Complexes Containing the Tripodal Tetraphosphine Ligand P(CH$_2$CH$_2$PMe$_2$)$_3$; Inorganic Chemistry, 1997, 36, 5984–5990.

Green, Malcolm L. H. et al: Arene Molybdenum Chemistry: Some π–Allyl, Dihydride, Dinitrogen, and Carbonly Derivatives, 1973, pp. 301–306.

Y. Mizobe et al., Preparation of Heterobimetallic Complexes with a Bridging Dinitrogen Ligand, [WX(PM$_{e2}$Ph)$_4$(μ–N$_2$)MCp$_2$Cl](M=Ti,X=Cl;M=Zr,Hf, X–I), and X–ray Structure of [WI(PMe$_2$Ph)$_3$(py)(μ–N$_2$)ZrCp$_2$Cl](py=Pyridine)$^{1"}$; Organometallics, 1994, 13, pp. 3764–3766.

H. Ishino et al.; "Novel Olefin Polymerization Catalyzed by Heterobimetallic Bridging Dinitrogen Complexes Containing Group 4 and Group 6 Transition Metals"; 2000 Kinki Chemical Society, Japan, pp. 228–229.

H. Ishino et al.; Synthesis, Structures, and Reactivities of Heterobimetallic Bridging Dinitrogen Complexes Containing Group 6 and Group 4 or 5 Transition Metals$^1$; Organometallics; 20, pp. 188–198.

Mizobe, Y.; Yokobayashi, Y.; Oshita, H.; Takahashi, T.; Hidai, M. Organometallics 1994, 13, 3764–3766.

* cited by examiner

Primary Examiner—David W. Wu
Assistant Examiner—Rip A. Lee
(74) Attorney, Agent, or Firm—Stevens, Davis, Miller & Mosher, L.L.P.

(57) ABSTRACT

A catalyst obtained by contacting a transition metal compound (A) of the general formula [1]:

$$[L_pX_oCp_jM(N_2)_nM'X_mL_l]X'_k \qquad [1],$$

wherein M and M' independently represent a transition metal of Group 3 to 10; X independently represents a hydrogen atom, halogen atom, a specific hydrocarbon group or the like; Cp is a cyclopentadienyl group; L represents a group which bonds to M or M' by lone pair of electrons or a π electron; X' represents a counter anion; k, l, m, o and p each independently represent an integer of 0 to 5; j represents an integer of 0 to 2; n+o+p+j≤6; n represents an integer of 1 to 3; and n+l+m≤6, with an organoaluminum, and an aluminoxane and/or boron compound, or with an aluminoxane and/or boron compound, and a process for producing an addition polymerization with the catalyst.

18 Claims, 1 Drawing Sheet

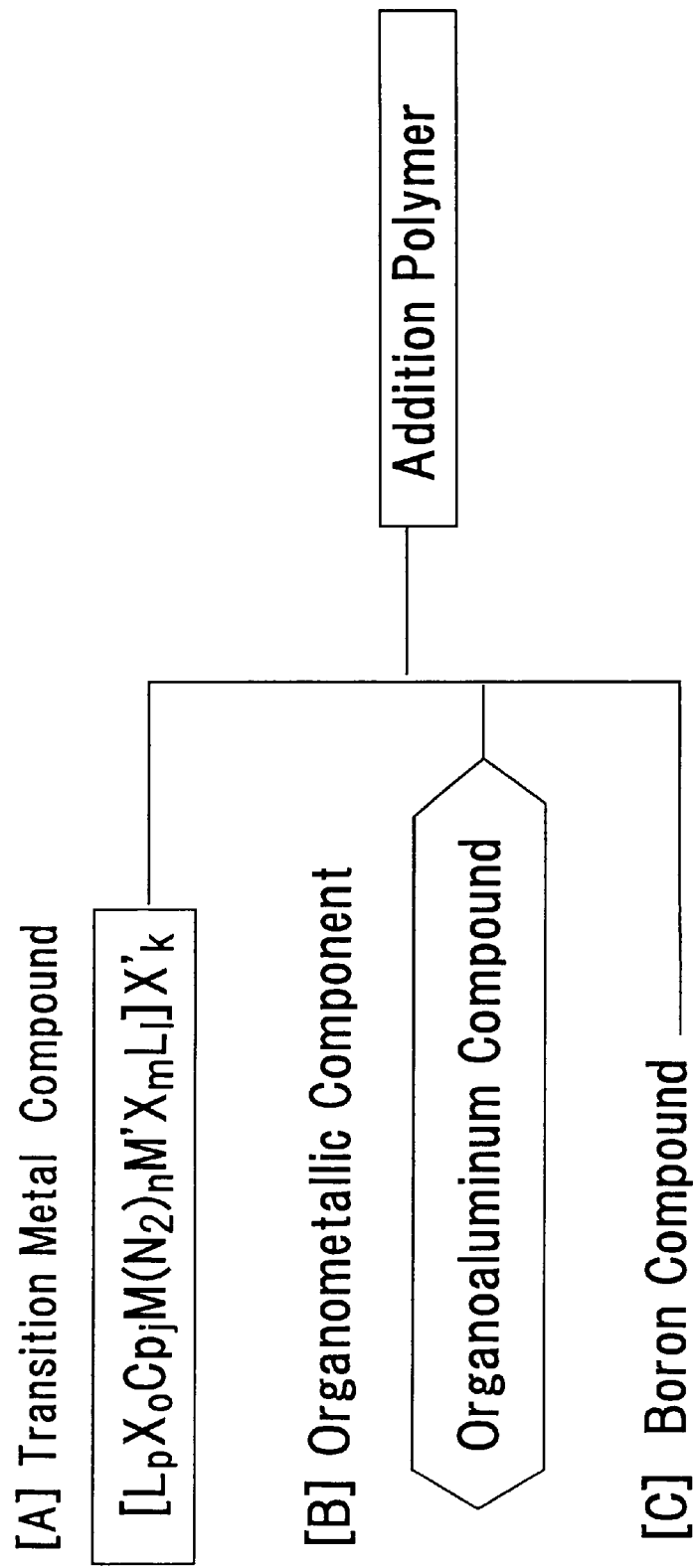

CATALYST COMPONENT AND CATALYST FOR ADDITION POLYMERIZATION, AND PROCESS FOR PRODUCING ADDITION POLYMER

CROSS-REFERENCE TO RELATED APPLICATION

This application is a continuation-in-part of U.S. application Ser. No. 09/986,472, filed Nov. 8, 2001, now abandoned, the entire disclosure of which is incorporated herein by reference

BACKGROUND OF THE INVENTION

1. Field of the Invention

The present invention relates to a catalyst component for addition polymerization, a catalyst for addition polymerization, and a process for producing an addition polymer. More particularly, the present invention relates to a catalyst component for addition polymerization composed of a transition metal compound having two transition metal atoms in one molecule, a catalyst for addition polymerization prepared by using the same, and a process for producing an addition polymer using this catalyst for addition polymerization.

2. Description of Related Arts

With respect to processes for producing an addition polymer such as an olefin polymer and the like using a transition metal compound which forms a single site catalyst such as a metallocene complex and the like, many reports have been reported. For example, JP60-245604A discloses a process for producing a copolymer of ethylene with an α-olefin using a metallocene complex and half metallocene complex.

SUMMARY OF THE INVENTION

A catalyst for addition polymerization used in the production of an addition polymer is more efficient when activity thereof is higher, and therefore, a catalyst for addition polymerization of high activity is required.

An object of the present invention is to provide a catalyst for addition polymerization having a high activity.

Another object of the present invention is to provide an process for producing an addition polymer with the catalyst.

Still another object of the present invention is to provide a transition metal compound useful as a catalyst component for addition polymerization.

Other objects and advantages of the present invention will be apparent from the description below.

Namely, the present invention relates to a catalyst for addition polymerization obtained by a process comprising bringing a transition metal compound(A) represented by the general formula [1]:

$$[L_pX_oCp_jM(N_2)_nM'X_mL_l]X'_k \quad [1],$$

wherein M and M' each independently represent a transition metal atom of Group 3 to 10 in the Periodic Table of the Elements; X each independently represents a hydrogen atom, halogen atom, alkyl group, aralkyl group, aryl group, substituted silyl group substituted with a hydrocarbon group, alkoxy group, aralkyloxy group, aryloxy group, di-substituted amino group substituted with two hydrocarbon groups, azido group, cyano group or isothiocyanate group; Cp is a group having a cyclopentadiene anion skeleton; L represents a group which bonds to M or M' by lone pair of electrons or a π electron; X' represents a counter anion; k, l, m, o and p each independently represent an integer of 0 to 5; j represents an integer of 0 to 2; n+o+p+j≦6; n represents an integer of 1 to 3; and n+l+m≦6, into contact with an organoaluminum compound selected from the group consisting of the following (B1), and at least one aluminoxane selected from the group consisting of the following (B2) and (B3) and/or the following (C), or with at least one aluminoxane selected from the group consisting of the following (B2) and (B3) and/or the following (C):

(B1) organoaluminum compounds of the general formula $E^1{}_aAlZ_{3-a}$, (B2) cyclic aluminoxanes having a structure of the general formula $\{-Al(E^2)-O-\}_b$, (B3) linear aluminoxanes having a structure of the general formula $E^3\{-Al(E^3)-O-\}_cAlE^3{}_2$, (wherein, each of $E^1$, $E^2$ and $E^3$ represents a hydrocarbon group; all $E^1$s, all $E^2$s or all $E^3$s may be the same or different; Z represents a hydrogen atom or halogen atom; all Zs may be the same or different; a represents a number satisfying 0<a<3; b represents an integer of 2 or more; and c represents an integer of 1 or more.), and (C) one or more boron compounds selected from the following (C1) to (C3):

(C1) boron compounds represented by the general formula $BQ^1Q^2Q^3$, (C2) boron compounds represented by the general formula $G^+(BQ^1Q^2Q^3Q^4)^-$, and (C3) boron compounds represented by the general formula $(L-H)+(BQ^1Q^2Q^3Q^4)$, wherein, B represents boron in trivalent state; $Q^1$ to $Q^4$ represent a halogen atom, hydrocarbon group, halogenated hydrocarbon group, substituted silyl group, alkoxy group or di-substituted amino group; they may be the same or different; $G^+$ represents an inorganic or organic cation; L represents a neutral Lewis base; and $(L-H)^+$ represents a Brønsted acid.

Further, the present invention relates to a process for producing an addition polymer using this catalyst.

Still further, the present invention relates to a transition metal compound (A), useful as a catalyst component for addition polymerization, represented by the general formula [1]:

$$[L_pX_oCp_jM(N_2)_nM'X_mL_l]X'_k \quad [1]$$

wherein, M and M' each independently represent a transition metal atom of Group 3 to 10 in the Periodic Table of the Elements; X each independently represents a hydrogen atom, halogen atom, alkyl group, aralkyl group, aryl group, substituted silyl group, alkoxy group, aralkyloxy group, aryloxy group, di-substituted amino group, azido group, cyano group or isothiocyanate group; Cp is a group having a cyclopentadiene anion skeleton; L represents a group which bonds to M or M' by lone pair of electrons or a π electron; X' represents a counter anion; k, l, m, o and p each independently represent an integer of 0 to 5; j represents an integer of 0 to 1; n represents an integer of 1 to 3; n+o+p+j is an integer of 6 or less; and n+l+m is an integer of 6 or less.

BRIEF DESCRIPTION OF THE DRAWING

FIG. 1 is a flow chart for helping understanding of the invention. This flow chart shows a typical example of embodiments of the invention, and the scope of the present invention is not restricted to this example at all.

The present invention will be illustrated in detail below.

DETAILED DESCRIPTION OF THE INVENTION (A) Transition Metal Compound

M and M' in a transition metal compound of the above-mentioned general formula [1] each independently represent a transition metal atom of Group 3 to 10 in the Periodic Table of the Elements (IUPAC Inorganic Chemistry Nomenclature revised edition, 1989).

M is preferably a transition metal atom of Group 3 to 5, more preferably a titanium atom, zirconium atom, hafnium atom, vanadium atom, niobium atom or tantalum atom, further preferably a titanium atom or zirconium atom.

M' is preferably a transition metal atom of Group 6 to 10, more preferably a chromium atom, molybdenum atom, tungsten atom, ruthenium atom, rhodium atom or palladium atom, further preferably a chromium atom, molybdenum atom or tungsten atom.

X in the above-mentioned general formula [1] represents a hydrogen atom, halogen atom, alkyl group, aralkyl group, aryl group, substituted silyl group, alkoxy group, aralkyloxy group, aryloxy group, di-substituted amino group, azido group, cyano group or isothiocyanate group, and all Xs may be the same or different.

Among these, a hydrogen atom, halogen atom, alkyl group, aralkyl group, aryl group, substituted silyl group, alkoxy group, aralkyloxy group, aryloxy group and di-substituted amino group are preferred.

As the halogen atom of the substituent X, a fluorine atom, chlorine atom, bromine atom, iodine atom and the like are listed.

The alkyl group of the substituent X is preferably an alkyl group having 1 to 20 carbon atoms, and examples thereof include a methyl group, ethyl group, n-propyl group, isopropyl group, n-butyl group, sec-butyl group, tert-butyl group, n-pentyl group, neopentyl group, isoamyl group, n-hexyl group, n-octyl group, n-decyl group, n-dodecyl group, n-pentadecyl group, n-eicosyl group and the like, and more preferable examples are a methyl group, ethyl group, isopropyl group, tert-butyl group and isoamyl group.

Any of these alkyl groups may be substituted with a halogen atom such as a fluorine atom, chlorine atom, bromine atom, iodine atom or the like. Examples of the alkyl group having 1 to 20 carbon atoms substituted with a halogen atom include a fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group, perbromoeicosyl group and the like.

Further, any of these alkyl groups may also be partially substituted with an alkoxy group such as a methoxy group, ethoxy group and or like, an aryloxy group such as a phenoxy group or the like, an aralkyloxy group such as a benzyloxy group or the like, etc.

The aralkyl group of the substituent X is preferably an aralkyl group having 7 to 20 carbon atoms, and examples thereof include a benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (3,5-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl) methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-tetradecylphenyl) methyl group, naphthylmethyl group, anthracenylmethyl group and the like, and a benzyl group is preferable.

Any of these aralkyl groups may also be partially substituted withahalogen atom such as a fluorine atom, chlorine atom, bromine atom, iodine atom or the like, an alkoxy group such as a methoxy group, ethoxy group or the like, an aryloxy group such as a phenoxy group or the like, an aralkyloxy group such as a benzyloxy group or the like, etc.

The aryl group of the substituent X is preferably an aryl group having 6 to 20 carbon atoms, and examples thereof include a phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group, anthracenyl group and the like, and a phenyl group is more preferable.

Any of these aryl groups may also be partially substituted with ahalogen atom such as a fluorine atom, chlorine atom, bromine atom, iodine atom or the like, an alkoxy group such as a methoxy group, ethoxy group or the like, an aryloxy group such as a phenoxy group or the like, an aralkyloxy group such as a benzyloxy group or the like, etc.

The substituted silyl group of the substituent X is a silyl group substituted with a hydrocarbon group, and examples of the hydrocarbon group include alkyl groups having 1 to 10 carbon atoms such as a methyl group, ethyl group, n-propyl group, isopropyl group, n-butyl group, sec-butyl group, tert-butyl group, isobutyl group, n-pentyl group, n-hexyl group, cyclohexyl group and the like, and aryl groups such as a phenyl group and the like, etc. As such substituted silyl group having 1 to 20 carbon atoms, for example, mono-substituted silyl groups having 1 to 20 carbon atoms such as a methylsilyl group, ethylsilyl group, phenylsilyl group and the like, di-substituted silyl groups having 2 to 20 carbon atoms such as a dimethylsilyl group, diethylsilyl group, diphenylsilyl group and the like, tri-substituted silyl groups such as a trimethylsilyl group, triethylsilyl group, tri-n-propylsilyl group, triisopropylsilyl group, tri-n-butylsilyl group, tri-sec-butylsilyl group, tri-tert-butylsilyl group, triisobutylsilyl group, tert-butyldimethylsilyl group, tri-n-pentylsilyl group, tri-n-hexylsilyl group, tricyclohexylsilyl group, triphenylsilyl group and the like, etc. are listed, and preferable are a trimethylsilyl group, tert-butyldimethylsilyl group and triphenylsilyl group.

Any of these substituted silyl groups may also be partially substituted with a halogen atom such as a fluorine atom, chlorine atom, bromine atom, iodine atom and the like, an alkoxy group such as a methoxy group, ethoxy group and the like, an aryloxy group such as a phenoxy group and the like, an aralkyloxy group such as a benzyloxy group and the like, etc.

The alkoxy group of the substituent X is preferably an alkoxy group having 1 to 20 carbon atoms, and examples thereof include a methoxy group, ethoxy group, n-propoxy group, isopropoxy group, n-butoxy group, sec-butoxy group, t-butoxy group, n-pentoxy group, neopentoxy group, n-hexoxy group, n-octoxy group, n-dodexoxy group, n-pentadexoxy group, n-icoxoxy group and the like, and more preferable are a methoxy group, ethoxy group, and t-butoxy group.

Any of these alkoxy groups may also be partially substituted with ahalogen atom such as a fluorine atom, chlorine atom, bromine atom, iodine atom or the like, an alkoxy group such as a methoxy group, ethoxy group or the like, an aryloxy group such as a phenoxy group or the like, an aralkyloxy group such as a benzyloxy group or the like, etc.

The aralkyloxy group of the substituent X is preferably an aralkyloxy group having 7 to 20 carbon atoms, and examples thereof include a benzyloxy group, (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (3,5-dimethylphenyl)methoxy group, (2,3,4-trimethylphenyl)methoxy group, (2,3,5-trimethylphenyl)methoxy group, (2,3,6-trimethylphenyl)methoxy group, (2,4,5-trimethylphenyl)methoxy group, (2,4,6-trimethylphenyl)methoxy group, (3,4,5-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-hexylphenyl)methoxy group, (n-octylphenyl)methoxy group, (n-decylphenyl)methoxy group, (n-tetradecylphenyl)methoxy group, naphthylmethoxy group, anthracenylmethoxy group and the like, and more preferable is a benzyloxy group.

Any of these aralkyloxy groups may also be partially substituted with a halogen atom such as a fluorine atom, chlorine atom, bromine atom, iodine atom or the like, an alkoxy group such as a methoxy group, ethoxy group or the like, an aryloxy group such as a phenoxy group or the like, an aralkyloxy group such as a benzyloxy group or the like, etc.

The aryloxy group of the substituent X is preferably an aryloxy group having 1 to 20 carbon atoms, and examples thereof include aryloxy groups having 6 to 20 carbon atoms such as a phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenyl group, tert-butylphenoxy group, n-hexylphenoxy group, n-octylphenoxy group, n-decylphenoxy group, n-tetradecylphenoxy group, naphthoxy group, anthracenoxy group and the like.

Any of these aryloxy groups may also be partially substituted with ahalogen atom such as a fluorine atom, chlorine atom, bromine atom, iodine atom or the like, an alkoxy group such as a methoxy group, ethoxy group or the like, an aryloxy group such as a phenoxy group or the like, an aralkyloxy group such as a benzyloxy group or the like, etc.

The di-substituted amino group of the substituent X is an aminogroupsubstitutedwithtwohydrocarbongroups, andexamples of the hydrocarbon group include alkyl groups having 1 to 10 carbon atoms such as a methyl group, ethyl group, n-propyl group, isopropyl group, n-butyl group, sec-butyl group, tert-butyl group, isobutyl group, n-pentyl group, n-hexyl group, cyclohexyl group and the like, and aryl groups such as a phenyl group, and the like. Examples of such di-substituted amino groups include a dimethylamino group, diethylamino group, di-n-propylamino group, diisopropylamino group, di-n-butylamino group, di-sec-butylamino group, di-tert-butylamino group, diosobutylamino group, tert-butylisopropylamino group, di-n-hexylamino group, di-n-octylamino group, di-n-decylamino group, diphenylamino group, bistrimethylsilylamino group, bis-tert-butyldimethylsilylamino group and the like, and preferable are a dimethylamino group, diethylamino group.

Cp in the general formula [1] represents a group having a cyclopentadiene anion skeleton.

As the group having a cyclopentadiene anion skeleton, there are listed $\eta^5$-(substituted)cyclopentadienyl group, $\eta^5$-(substituted)indenyl group, $\eta^5$-(substituted)fluorenyl group and the like. Specific examples thereof are a $\eta^5$-cyclopentadienyl group, $\eta^5$-methylcyclopentadienyl group, $\eta^5$-dimethylcyclopentadienyl group, $\eta^5$-trimethylcyclopentadienyl group, $\eta^5$-tetramethylcyclopentadienyl group, $\eta^5$-pentamethylcyclopentadienyl group, $\eta^5$-ethylcyclopentadienyl group, $\eta^5$-n-propylcyclopentadienyl group, $\eta^5$-isopropylcyclopentadienyl group, $\eta^5$-n-butylcyclopentadienyl group, $\eta^5$-sec-butylcyclopentadienyl group, $\eta^5$-tert-butylcyclopentadienyl group, $\eta^5$-n-pentylcyclopentadienyl group, $\eta^5$-neopentylcyclopentadienyl group, $\eta^5$-n-hexylcyclopentadienyl group, $\eta^5$-n-octylcyclopentadienyl group, $\eta^5$-phenylcyclopentadienyl group, $\eta^5$-naphthylcyclopentadienyl group, $\eta^5$-trimethylsilylcyclopentadienyl group, $\eta^5$-triethylsilylcyclopentadienyl group, $\eta^5$-tert-butyldimethylsilylcyclopentadienyl group, $\eta^5$-indenyl group, η⁵-methylindenyl group, η⁵-dimethylindenyl group, η⁵-ethylindenyl group, η⁵-n-propylindenyl group, η⁵-isopropylindenyl group, η⁵-n-butylindenyl group, η⁵-sec-butylindenyl group, η⁵-tert-butylindenyl group, η⁵-n-pentylindenyl group, η⁵-neopentylindenyl group, η⁵-n-hexylindenyl group, η⁵-n-octylindenyl group, η⁵-n-decylindenyl group, η⁵-phenylindenyl group, η⁵-methylphenylindenyl group, η⁵-naphthylindenyl group, η⁵-trimethylsilylindenyl group, η⁵-triethylsilylindenyl group, η⁵-tert-butyldimethylsilylindenyl group, η⁵-tetrahydroindenyl group, η⁵-fluorenyl group, η⁵-methylfluorenyl group, η⁵-dimethylfluorenyl group, η⁵-ethylfluorenyl group, η⁵-diethylfluorenyl group, η⁵-n-propylfluorenyl group, η⁵-di-n-propylfluorenyl group, η⁵-isopropylfluorenyl group, η⁵-diisopropylfluorenyl group, η⁵-n-butylfluorenyl group, η⁵-sec-butylfluorenyl group, η⁵-tert-butylfluorenyl group, η⁵-di-n-butylfluorenyl group, η⁵-di-sec-butylfluorenyl group, η⁵-di-tert-butylfluorenyl group, η⁵-n-pentylfluorenyl group, η⁵-neopentylfluorenyl group, η⁵-n-hexylfluorenyl group, η⁵-n-octylfluorenyl group, η⁵-n-decylfluorenyl group, η⁵-n-dodecylfluorenyl group, η⁵-phenylfluorenyl group, η⁵-di-phenylfluorenyl group, η⁵-methylphenylfluorenyl group, η⁵-naphthylfluorenyl group, η⁵-trimethylsilylfluorenyl group, η⁵-bis-trimethylsilylfluorenyl group, η⁵-triethylsilylfluorenyl group, η⁵-tert-butyldimethylsilylfluorenyl group and the like, and preferable are a η⁵-cyclopentadienyl group, η⁵-methylcyclopentadienyl group, η⁵-tert-butylcyclopentadienyl group, η⁵-tetramethylcyclopentadienyl group, η⁵-pentamethylcyclopentadienyl group, η⁵-indenyl group and η⁵-fluorenyl group.

Herein-after, "η⁵-" is sometimes omitted.

X' in the above-mentioned general formula [1] represents a counter anion, and is an anionic group which is not covalent-bonded to but free ionically from M, and for example, conjugated bases of Brønsted acids are listed. X' is preferably $F^-$, $Cl^-$, $Br^-$, $I^-$, $BF_4^-$, $B(phenyl)_4^-$ or $PF_6^-$.

L in the above-mentioned general formula [1] represents a group which bonds to M or M' by lone pair of electrons or π electron.

The group which bonds to M or M' by lone pair of electrons is a neutral ligand which bonds to M or M' by a coordination bond, and examples thereof include ethers such as diethyl ether, tetrahydrofuran, diethoxyethane; amines such as triethylamine, N,N,N',N'-tetramethylethylenediamine; pyridines such as pyridine, 2,6-dimethylpyridine, quinoline; phosphines such as trimethylphosphine, triethylphosphine, triphenylphosphine, dimethylphenylphosphine, methyldiphenylphosphine, 1,2-bis(dimethylphosphino)ethane, 1,2-bis(diethylphosphino)ethane, 1,2-bis(diphenylphosphino)ethane, 1,3-bis(diphenylphosphino)propane; nitrites such as acetonitrile, benzonitrile and the like, an end-on type nitrogen molecule and carbon mono-oxide, and the like, and preferable are tetrahydrofuran, N,N,N',N'-tetramethylethylenediamine, pyridine, dimethylphenylphosphine, 1,2-bis(dimethylphosphino)ethane, 1,2-bis(diethylphosphino)ethane, 1,2-bis(diphenylphosphino)ethane, 1,3-bis(diphenylphosphino)propane, acetonitrile and carbon mono-oxide.

The group which bonds to M or M' by a π electron is a neutral ligand which bonds to M or M' by a multi bonding orbital, and examples thereof include olefins such as ethylene, propylene and the like, dienes such as butadiene, 2,4-hexadiene, 1,4-diphenylbutadiene; ketones such as acetone, benzophenone; a side-on type nitrogen molecule, and the like, and preferable are olefins and dienes, and more preferable are ethylene, butadiene, 2,4-hexadiene and 1,4-diphenylbutadiene.

k, l, m, o and p each independently represent an integer of 0 to 5, j is an integer of 0 to 2, preferably 0 or 1, more preferably 1, and n represents an integer of 1 to 3 in the above-mentioned general formula [1]. 1, m, o, j and p are preferably selected so as to satisfy q≧o+n; r≧m+n; n+o+p+j≦6 and n+l+m≦6 (preferably, n+m+l=6) when group numbers of M and M' in the Periodic Table are represented by q and r, respectively. k is preferably selected so as to satisfy k=s+t−o−j−m−2 when the oxidation numbers of M and M' are represented by s and t, respectively.

As the partial structure $M(N_2)_nM'$ in a transition metal compound of the above-mentioned general formula [1], the following structures are exemplified.

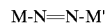
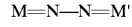

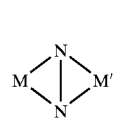
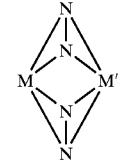

A transition metal compound of the general formula [1] used in the present invention is produced by, for example, a method described in Organometallics, Vol. 13, p.3764–3766 (1994).

Specific examples of a compound of the general formula [1] include transition metal compounds such as
[chlorotetrakis(trimethylphosphine)tungsten](μ-dinitrogen)[trichlorotitanium],
[chlorotris(trimethylphosphine)(pyridine)tungsten](μ-dinitrogen)[trichlorotitanium],
[chlorotetrakis(triethylphosphine)tungsten] (μ-dinitrogen)[trichlorotitanium],
[chlorotris(triethylphosphine)(pyridine)tungsten](μ-dinitrogen) [trichlorotitanium],
[chlorotetrakis(triphenylphosphine)tungsten] (μ-dinitrogen)[trichlorotitanium],
[chlorotris(triphenylphosphine)(pyridine)tungsten](μ-dinitrogen) [trichlorotitanium],
[chlorotetrakis(dimethylphenylphosphine)tungsten](μ-dinitrogen) [trichlorotitanium],
[chlorotris(dimethylphenylphosphine)(pyridine)tungsten](μ-dinitrogen) [trichlorotitanium],
[chlorotetrakis(methyldiphenylphosphine)tungsten](μ-dinitrogen) [trichlorotitanium],
[chlorotris(methyldiphenylphosphine)(pyridine)tungsten](μ-dinitrogen) [trichlorotitanium],
[chlorobis{1,2-bis(dimethylphosphino)ethane}tungsten](μ-dinitrogen) [trichlorotitanium],
[chlorobis{1,2-bis(diethylphosphino)ethane}tungsten](μ-dinitrogen) [trichlorotitanium],
[chlorobis{1,2-bis(diphenylphosphino)ethane}tungsten](μ-dinitrogen)[trichlorotitanium],
[chlorobis{1,3-bis(diphenylphosphino)propane}tungsten](μ-dinitrogen)[trichlorotitanium],
[chlorotris(trimethylphosphine)(2,6-dimethylpyridine)tungsten](μ-dinitrogen) [trichlorotitanium],
[chlorotris(triethylphosphine)(2,6-dimethylpyridine)tungsten](μ-dinitrogen) [trichlorotitanium],

[chlorotris(triphenylphosphine)(2,6-dimethylpyridine)tungsten](μ-dinitrogen) [trichlorotitanium],
[chlorotris(dimethylphenylphosphine)(2,6-dimethylpyridine)tungsten](1-dinitrogen) [trichlorotitanium],
[chlorotris(trimethylphosphine)(quinoline)tungsten] (μ-dinitrogen) [trichlorotitanium],
[chlorotris(triethylphosphine)(quinoline)tungsten] (μ-dinitrogen) [trichlorotitanium],
[chlorotris(triphenylphosphine)(quinoline)tungsten] (μ-dinitrogen) [trichlorotitanium],
[chlorotris(dimethylphenylphosphine)(quinoline)tungsten] (μ-dinitrogen) [trichlorotitanium],
[chloro(tetrahydrofuran)tris(trimethylphosphine)tungsten] (μ-dinitrogen) [trichlorotitanium],
[chloro(tetrahydrofuran)tris(triethylphosphine)tungsten] (μ-dinitrogen) [trichlorotitanium],
[chloro(tetrahydrofuran)tris(triphenylphosphine)tungsten] (1-dinitrogen)[trichlorotitanium],
[chloro(tetrahydrofuran)tris(dimethylphenylphosphine)tungsten](μ-dinitrogen) [trichlorotitanium],
[chloro(diethyl ether)tris(dimethylphosphine)tungsten] (μ-dinitrogen)[trichlorotitanium], [chloro(diethyl ether)tris(triethylphosphine)tungsten] (μ-dinitrogen) [trichlorotitanium], [chloro(diethyl ether)tris(triphenylphosphine)tungsten] (μ-dinitrogen) [trichlorotitanium], [chloro(diethyl ether)tris(dimethylphenylphosphine)tungsten] (μ-dinitrogen) [trichlorotitanium],
[chloro(acetonitrile)tris(trimethylphosphine)tungsten] (μ-dinitrogen) [trichlorotitanium],
[chloro(acetonitrile)tris(triethylphosphine)tungsten] (μ-dinitrogen) [trichlorotitanium],
[chloro(acetonitrile)tris(triphenylphosphine)tungsten] (μ-dinitrogen) [trichlorotitanium],
[chloro(acetonitrile)tris(dimethylphenylphosphine)tungsten] (μ-dinitrogen) [trichlorotitanium],
[chloro(benzonitrile)tris(trimethylphosphine)tungsten] (μ-dinitrogen) [trichlorotitanium],
[chloro(benzonitrile)tris(triethylphosphine)tungsten] (μ-dinitrogen) [trichlorotitanium],
[chloro(benzonitrile)tris(triphenylphosphine)tungsten] (μ-dinitrogen) [trichlorotitanium],
[chloro(benzonitrile)tris(dimethylphenylphosphine)tungsten] (μ-dinitrogen) [trichlorotitanium],
[chloro(carbonyl)tris(trimethylphosphine)tungsten] (μ-dinitrogen) [trichlorotitanium],
[chloro(carbonyl)tris(triethylphosphine)tungsten] (μ-dinitrogen) [trichlorotitanium],
[chloro(carbonyl)tris(triphenylphosphine)tungsten] (μ-dinitrogen) [trichlorotitanium],
[chloro(carbonyl)tris(dimethylphenylphosphine)tungsten] (μ-dinitrogen) [trichlorotitanium],
[chloro(dimethoxyethane)bis(trimethylphosphine)tungsten] (μ-dinitrogen)[trichlorotitanium],
[chloro(dimethoxyethane)bis(triethylphosphine)tungsten] (μ-dinitrogen)[trichlorotitanium],
[chloro(dimethoxyethane)bis(triphenylphosphine)tungsten] (μ-dinitrogen)[trichlorotitanium],
[chloro(dimethoxyethane)bis(dimethylphenylphosphine)tungsten](μ-dinitrogen) [trichlorotitanium],
[chloro(dimethoxyethane)bis(methyldiphenylphosphine)tungsten](μ-dinitrogen)[trichlorotitanium],
[chloro(diphenylphosphinoethane)(dimethoxyethane)tungsten] (μ-dinitrogen) [trichlorotitanium],
[chloro(diphenylphosphinopropane)(dimethoxyethane)tungsten] (μ-dinitrogen) [trichlorotitanium],
[chloro(N,N,N',N'-tetramethylethylenediamine)bis(trimethylphosphine)tungsten] (μ-dinitrogen) [trichlorotitanium],
[chloro(N,N,N',N'-tetramethylethylenediamine)bis(triethylphosphine)tungsten] (μ-dinitrogen) [trichlorotitanium],
[chloro(N,N,N',N'-tetramethylethylenediamine)bis(triphenylphosphine)tungsten] (μ-dinitrogen) [trichlorotitanium],
[chloro(N,N,N',N'-tetramethylethylenediamine)bis(dimethylphenylphosphine)tungsten] (μ-dinitrogen) [trichlorotitanium],
[chloro(N,N,N',N'-tetramethylethylenediamine)bis(methyldiphenylphosphine)tungsten] (μ-dinitrogen) [trichlorotitanium],
[chloro(N,N,N',N'-tetramethylethylenediamine)(diphenylphosphinoethane)tungsten] (μ-dinitrogen) [trichlorotitanium],
[chloro(N,N,N',N'-tetramethylethylenediamine)(diphenylphosphinopropane)tungsten] (μ-dinitrogen) [trichlorotitanium] and the like, compounds obtained by substituting tungsten in these compounds by molybdenum, chromium, ruthenium, rhodium or palladium, compounds obtained by substituting titanium in these compounds by zirconium, hafnium, vanadium, niobium, tantalum or scandium, and compounds obtained by substituting chloro in these compounds by fluoro, bromo, iodo, methyl, benzyl, methoxy or phenoxy.

Specific examples of the transition metal compound represented by the general formula [1] in which j is 1, include transition metal compounds such as
[chlorotetrakis(trimethylphosphine)tungsten] (μ-dinitrogen) [dichloro(cyclopentadienyl)titanium],
[chlorotris(trimethylphosphine)tungsten] (μ-dinitrogen) [dichloro(cyclopentadienyl)titanium],
[chlorotetrakis(triethylphosphine)(pyridine)tungsten] (μ-dinitrogen) [dichloro(cyclopentadienyl)titanium],
[chlorotris(triethylphosphine)(pyridine)tungsten] (μ-dinitrogen) [dichloro(cyclopentadienyl)titanium],
[chlorotetrakis(triphenylphosphine)tungsten] (μ-dinitrogen) [dichloro(cyclopentadienyl)titanium],
[chlorotris(triphenylphosphine)(pyridine)tungsten] (μ-dinitrogen) [dichloro(cyclopentadienyl)titanium],
[chlorotetrakis(dimethylphenylphosphine)tungsten] (μ-dinitrogen) [dichloro(cyclopentadienyl)titanium],
[chlorotris(dimethylphenylphosphine)(pyridine)tungsten] (μ-dinitrogen) [dichloro(cyclopentadienyl)titanium],
[chlorotetrakis(methyldiphenylphosphine)tungsten] (μ-dinitrogen) [dichloro(cyclopentadienyl)titanium],
[chlorotris(methyldiphenylphosphine)(pyridine)tungsten] (μ-dinitrogen) [dichloro(cyclopentadienyl)titanium],
[chlorobis{1,2-bis(dimethylphosphino)ethane}tungsten] (μ-dinitrogen) [dichloro(cyclopentadienyl)titanium],
[chlorobis{1,2-bis(diethylphosphino)ethane}tungsten] (μ-dinitrogen) [dichloro(cyclopentadienyl)titanium],
[chlorobis{1,2-bis(diphenylphosphino)ethane}tungsten] (μ-dinitrogen) [dichloro(cyclopentadienyl)titanium],
[chlorobis{1,3-bis(diphenylphosphino)propane}tungsten] (μ-dinitrogen) [dichloro(cyclopentadienyl)titanium],
[chlorotris(trimethylphosphine)(2,6-dimethylpyridine)tungsten(μ-dinitrogen) [dichloro(cyclopentadienyl)titanium],
[chlorotris(triethylphosphine)(2,6-dimethylpyridine)tungsten(μ-dinitrogen) [dichloro(cyclopentadienyl)titanium],
[chlorotris(triphenylphosphine)(2,6-dimethylpyridine)tungsten(μ-dinitrogen) [dichloro(cyclopentadienyl)titanium],

[chlorotris(dimethylphenylphosphine)(2,6-dimethylpyridine)tungsten($\mu$-dinitrogen) [dichloro(cyclopentadienyl) titanium],
[chlorotris (trimethylphosphine)(quinoline)tungsten($\mu$-dinitrogen) [dichloro(cyclopentadienyl)titanium],
[chlorotris(triethylphosphine)(quinoline)tungsten($\mu$-dinitrogen) [dichloro(cyclopentadienyl)titanium],
[chlorotris(triphenylphosphine)(quinoline)tungsten($\mu$-dinitrogen) [dichloro(cyclopentadienyl)titanium],
[chlorotris(dimethylphenylphosphine)(quinoline)tungsten($\mu$-dinitrogen) [dichloro(cyclopentadienyl)titanium],
[chloro(tetrahydrofuran)tris(trimethylphosphine)tungsten($\mu$-dinitrogen) [dichloro(cyclopentadienyl)titanium],
[chloro(tetrahydrofuran)tris(triethylphosphine)tungsten($\mu$-dinitrogen) [dichloro(cyclopentadienyl)titanium],
[chloro(tetrahydrofuran)tris(triphenylphosphine)tungsten($\mu$-dinitrogen) [dichloro(cyclopentadienyl)titanium],
[chloro(tetrahydrofuran)tris(dimethylphenylphosphine)tungsten($\mu$-dinitrogen) [dichloro(cyclopentadienyl) titanium],
[chloro(diethyl ether)tris(trimethylphosphine)tungsten($\mu$-dinitrogen) [dichloro(cyclopentadienyl)titanium],
[chloro(diethyl ether)tris(triethylphosphine)tungsten($\mu$-dinitrogen) [dichloro(cyclopentadienyl)titanium],
[chloro(diethyl ether)tris(triphenylphosphine)tungsten($\mu$-dinitrogen) [dichloro(cyclopentadienyl)titanium],
[chloro(diethyl ether)tris(dimethylphenylphosphine)tungsten($\mu$-dinitrogen) [dichloro(cyclopentadienyl)titanium],
[chloro(acetonitrile)tris(trimethylphosphine)tungsten($\mu$-dinitrogen) [dichloro(cyclopentadienyl)titanium],
[chloro(acetonitrile)tris(triethylphosphine)tungsten($\mu$-dinitrogen) [dichloro(cyclopentadienyl)titanium],
[chloro(acetonitrile)tris(triphenylphosphine)tungsten($\mu$-dinitrogen) [dichloro(cyclopentadienyl)titanium],
[chloro(acetonitrile)tris(dimethylphenylphosphine)tungsten ($\mu$-dinitrogen) [dichloro(cyclopentadienyl)titanium],
[chloro(benzonitrile)tris(trimethylphosphine)tungsten($\mu$-dinitrogen) [dichloro(cyclopentadienyl)titanium],
[chloro(benzonitrile)tris(triethylphosphine)tungsten($\mu$-dinitrogen) [dichloro(cyclopentadienyl)titanium],
[chloro(benzonitrile)tris(triphenylphosphine)tungsten($\mu$-dinitrogen) [dichloro(cyclopentadienyl)titanium],
[chloro(benzonitrile)tris(dimethylphenylphosphine)tungsten($\mu$-dinitrogen) [dichloro(cyclopentadienyl) titanium],
[chloro(carbonyl)tris(trimethylphosphine)tungsten($\mu$-dinitrogen) [dichloro(cyclopentadienyl)titanium],
[chloro(carbonyl)tris(triethylphosphine)tungsten($\mu$-dinitrogen) [dichloro(cyclopentadienyl)titanium],
[chloro(carbonyl)tris(triphenylphosphine)tungsten($\mu$-dinitrogen) [dichloro(cyclopentadienyl)titanium],
[chloro(carbonyl)tris(dimethylphenylphosphine)tungsten($\mu$-dinitrogen) [dichloro(cyclopentadienyl)titanium],
[chloro(dimethoxyethane)bis(trimethylphosphine)tungsten ($\mu$-dinitrogen) [dichloro(cyclopentadienyl)titanium],
[chloro(dimethoxyethane)bis(triethylphosphine)tungsten($\mu$-dinitrogen) [dichloro(cyclopentadienyl)titanium],
[chloro(dimethoxyethane)bis(triphenylphosphine)tungsten ($\mu$-dinitrogen) [dichloro(cyclopentadienyl)titanium],
[chloro(dimethoxyethane)bis(dimethylphenylphosphine)tungsten($\mu$-dinitrogen) [dichloro(cyclopentadienyl) titanium],
[chloro(dimethoxyethane)bis(methyldiphenylphosphine)tungsten($\mu$-dinitrogen) [dichloro(cyclopentadienyl) titanium],
[chloro(diphenylphosphinoethane)(dimethoxyethane)tungsten($\mu$-dinitrogen) [dichloro(cyclopentadienyl) titanium],
[chloro(diphenylphosphinopropane)(dimethoxyethane)tungsten($\mu$-dinitrogen) [dichloro(cyclopentadienyl) titanium],
[chloro(N,N,N',N'-tetramethylethylenediamine)bis(trimethylphosphine)tungsten] ($\mu$-dinitrogen) [dichloro(cyclopentadienyl)titanium],
[chloro(N,N,N',N'-tetramethylethylenediamine)bis(triethylphosphine)tungsten] ($\mu$-dinitrogen) [dichloro(cyclopentadienyl)titanium],
[chloro(N,N,N',N'-tetramethylethylenediamine)bis(triphenylphosphine)tungsten] ($\mu$-dinitrogen) [dichloro(cyclopentadienyl)titanium],
[chloro(N,N,N',N'-tetramethylethylenediamine)bis(dimethylphenylphosphine)tungsten] ($\mu$-dinitrogen) [dichloro(cyclopentadienyl)titanium],
[chloro(N,N,N',N'-tetramethylethylenediamine)bis(methyldiphenylphosphine)tungsten] ($\mu$-dinitrogen) [dichloro(cyclopentadienyl)titanium],
[chloro(N,N,N',N'-tetramethylethylenediamine)(diphenylphosphinoethane)tungsten] ($\mu$-dinitrogen) [dichloro(cyclopentadienyl)titanium],
[chloro(N,N,N',N'-tetramethylethylenediamine)(diphenylphosphinopropane)tungsten] ($\mu$-dinitrogen) [dichloro(cyclopentadienyl)titanium], compounds obtained by substituting tungsten in these compounds by molybdenum, chromium, ruthenium, rhodium or palladium, compounds obtained by substituting titanium in these compounds by zirconium, hafnium, vanadium, niobium, tantalum or scandium, compounds obtained by substituting dichloro in these compounds by difluoro, dibromo, diiodo, dimethyl, dibenzyl, dimethoxy, diphenoxy, 1,3-butadiene, 2,4-hexadiene, diphenyl-1,3-butadiene, (chloro)(methyl), (benzyl)(chloro), (chloro)(methoxy) or (chloro)(phenoxy), transition metal compounds obtained by substituting cyclopentadienyl in these compounds by methylcyclopentadienyl, dimethylcyclopentadienyl, trimethylcyclopentadienyl, tetramethylcyclopentadienyl, n-butylcyclopentadienyl, tert-butyldimethylsilylcyclopentadienyl, indenyl, tetrahydroindenyl, fluorenyl or octahydrofluorenyl.

Further, specific examples of the transition metal compound of the general formula [1] in which j is 2, include transition metal compounds such as
[chlorotetrakis(trimethylphosphine)tungsten] ($\mu$-dinitrogen) [chlorobis(cyclopentadienyl)titanium],
[chlorotris(trimethylphosphine)tungsten] ($\mu$-dinitrogen) [chlorobis(cyclopentadienyl)titanium],
[chlorotetrakis(triethylphosphine)(pyridine)tungsten] ($\mu$-dinitrogen) [chlorobis(cyclopentadienyl)titanium],
[chlorotris(triethylphosphine)(pyridine)tungsten] ($\mu$-dinitrogen) [chlorobis(cyclopentadienyl)titanium),
[chlorotetrakis(triphenylphosphine)tungsten] ($\mu$-dinitrogen) [chlorobis(cyclopentadienyl)titanium),
[chlorotris(triphenylphosphine)(pyridine)tungsten] ($\mu$-dinitrogen) [chlorobis(cyclopentadienyl)titanium),
[chlorotetrakis(dimethylphenylphosphine)tungsten] ($\mu$-dinitrogen) [chlorobis(cyclopentadienyl)titanium),
[chlorotris(dimethylphenylphosphine)(pyridine)tungsten] ($\mu$-dinitrogen) [chlorobis(cyclopentadienyl)titanium),
[chlorotetrakis(methyldiphenylphosphine)tungsten] ($\mu$-dinitrogen) [chlorobis(cyclopentadienyl)titanium),
[chlorotris(methyldiphenylphosphine)(pyridine)tungsten] ($\mu$-dinitrogen) [chlorobis(cyclopentadienyl)titanium),
[chlorobis{1,2-bis(dimethylphosphino)ethane}tungsten] ($\mu$-dinitrogen) [chlorobis(cyclopentadienyl)titanium),
[chlorobis{1,2-bis(diethylphosphino)ethane}tungsten] ($\mu$-dinitrogen)[chlorobis(cyclopentadienyl)titanium),

[chlorobis{1,2-bis(diphenylphosphino)ethane}tungsten] (μ-dinitrogen)[chlorobis(cyclopentadienyl)titanium),
[chlorobis{1,3-bis(diphenylphosphino)propane}tungsten] (μ-dinitrogen)[chlorobis(cyclopentadienyl)titanium],
[chlorotris(trimethylphosphine)(2,6-dimethylpyridine) tungsten(μ-dinitrogen)[chlorobis(cyclopentadienyl) titanium),
[chlorotris(triethylphosphine) (2,6-dimethylpyridine) tungsten(1-dinitrogen)[chlorobis(cyclopentadienyl) titanium],
[chlorotris(triphenylphosphine)(2,6-dimethylpyridine) tungsten(μ-dinitrogen)[chlorobis(cyclopentadienyl) titanium],
[chlorotris(dimethylphenylphosphine)(2,6-dimethylpyridine)tungsten(μ-dinitrogen) [chlorobis (cyclopentadienyl) titanium],
[chlorotris (trimethylphosphine)(quinoline)tungsten(μ-dinitrogen) [chlorobis(cyclopentadienyl)titanium],
[chlorotris(triethylphosphine)(quinoline)tungsten(μ-dinitrogen) [chlorobis(cyclopentadienyl)titanium],
[chlorotris(triphenylphosphine)(quinoline)tungsten(μ-dinitrogen) [chlorobis(cyclopentadienyl)titanium],
[chlorotris(dimethylphenylphosphine)(quinoline)tungsten (μ-dinitrogen) [dichloro(cyclopentadienyl)titanium],
[chloro(tetrahydrofuran)tris(trimethylphosphine)tungsten (μ-dinitrogen) [dichloro(cyclopentadienyl)titanium],
[chloro(tetrahydrofuran)tris(triethylphosphine)tungsten(μ-dinitrogen) [chlorobis(cyclopentadienyl)titanium],
[chloro(tetrahydrofuran)tris(triphenylphosphine)tungsten(μ-dinitrogen) [chlorobis(cyclopentadienyl)titanium],
[chloro(tetrahydrofuran)tris(dimethylphenylphosphine) tungsten(μ-dinitrogen) [chlorobis(cyclopentadienyl) titanium],
[chloro(diethyl ether)tris(trimethylphosphine)tungsten(μ-dinitrogen) [chlorobis(cyclopentadienyl)titanium],
[chloro(diethyl ether)tris(triethylphosphine)tungsten(μ-dinitrogen) [chlorobis(cyclopentadienyl)titanium],
[chloro(diethyl ether)tris(triphenylphosphine)tungsten(μ-dinitrogen) [chlorobis(cyclopentadienyl)titanium],
[chloro(diethyl ether)tris (dimethylphenylphosphine) tungsten(1-dinitrogen) [chlorobis(cyclopentadienyl)titanium],
[chloro(acetonitrile)tris(trimethylphosphine)tungsten(μ-dinitrogen) [chlorobis(cyclopentadienyl)titanium],
[chloro(acetonitrile)tris(triethylphosphine)tungsten(μ-dinitrogen) [chlorobis(cyclopentadienyl)titanium],
[chloro(acetonitrile)tris(triphenylphosphine)tungsten(μ-dinitrogen) [chlorobis(cyclopentadienyl)titanium],
[chloro(acetonitrile)tris(dimethylphenylphosphine)tungsten (μ-dinitrogen) [chlorobis(cyclopentadienyl)titanium],
[chloro(benzonitrile)tris(trimethylphosphine)tungsten(μ-dinitrogen) [chlorobis(cyclopentadienyl)titanium],
[chloro(benzonitrile)tris(triethylphosphine)tungsten(μ-dinitrogen) [chlorobis(cyclopentadienyl)titanium],
[chloro(benzonitrile)tris(triphenylphosphine)tungsten(μ-dinitrogen) [chlorobis(cyclopentadienyl)titanium],
[chloro(benzonitrile)tris(dimethylphenylphosphine) tungsten(μ-dinitrogen) [chlorobis(cyclopentadienyl) titanium],
[chloro(carbonyl)tris(trimethylphosphine)tungsten(μ-dinitrogen)[chlorobis(cyclopentadienyl)titanium],
[chloro(carbonyl)tris(triethylphosphine)tungsten(μ-dinitrogen)[chlorobis(cyclopentadienyl)titanium],
[chloro(carbonyl)tris(triphenylphosphine)tungsten(μ-dinitrogen)[chlorobis(cyclopentadienyl)titanium],
[chloro(carbonyl)tris(dimethylphenylphosphine)tungsten(μ-dinitrogen)[chlorobis(cyclopentadienyl)titanium],
[chloro(dimethoxyethane)bis(trimethylphosphine)tungsten (μ-dinitrogen)[chlorobis(cyclopentadienyl)titanium],
[chloro(dimethoxyethane)bis(triethylphosphine)tungsten(μ-dinitrogen)[chlorobis(cyclopentadienyl)titanium],
[chloro(dimethoxyethane)bis(triphenylphosphine)tungsten (μ-dinitrogen)[chlorobis(cyclopentadienyl)titanium],
[chloro(dimethoxyethane)bis(dimethylphenylphosphine) tungsten(μ-dinitrogen) [chlorobis(cyclopentadienyl) titanium],
[chloro(dimethoxyethane)bis(methyldiphenylphosphine) tungsten(μ-dinitrogen)[chlorobis(cyclopentadienyl) titanium],
[chloro(diphenylphosphinoethane)(dimethoxyethane) tungsten(μ-dinitrogen) [chlorobis(cyclopentadienyl) titanium],
[chloro(diphenylphosphinopropane)(dimethoxyethane) tungsten(μ-dinitrogen) [chlorobis(cyclopentadienyl) titanium],
[chloro(N,N,N',N'-tetramethylethylenediamine)bis (trimethylphosphine)tungsten] (μ-dinitrogen) [chlorobis(cyclopentadienyl)titanium],
[chloro(N,N,N',N'-tetramethylethylenediamine)bis (triethylphosphine)tungsten] (μ-dinitrogen) [chlorobis(cyclopentadienyl)titanium],
[chloro(N,N,N',N'-tetramethylethylenediamine)bis (triphenylphosphine)tungsten] (μ-dinitrogen) [chlorobis(cyclopentadienyl)titanium],
[chloro(N,N,N',N'-tetramethylethylenediamine)bis (dimethylphenylphosphine)tungsten] (μ-dinitrogen) [chlorobis(cyclopentadienyl)titanium],
[chloro(N,N,N',N'-tetramethylethylenediamine)bis (methyldiphenylphosphine)tungsten] (μ-dinitrogen) [chlorobis(cyclopentadienyl)titanium],
[chloro(N,N,N',N'-tetramethylethylenediamine) (diphenylphosphinoethane)tungsten] (μ-dinitrogen) [chlorobis(cyclopentadienyl)titanium],
[chloro(N,N,N',N'-tetramethylethylenediamine) (diphenylphosphinopropane)tungsten] (μ-dinitrogen) [chlorobis(cyclopentadienyl)titanium], compounds obtained by substituting tungsten in these compounds by molybdenum, chromium, ruthenium, rhodium or palladium, compounds obtained by substituting titanium in these compounds by zirconium, hafnium, vanadium, niobium, tantalum or scandium, compounds obtained by substituting chloro in these compounds by fluoro, bromo, iodo, methyl, benzyl, methoxy or phenoxy, transition metal compounds obtained by substituting cyclopentadienyl in these compounds by methylcyclopentadienyl, dimethylcyclopentadienyl, trimethylcyclopentadienyl, tetramethylcyclopentadienyl, n-butylcyclopentadienyl, tert-butyldimethylsilylcyclopentadienyl, indenyl, tetrahydroindenyl, fluorenyl or octahydrofluorenyl.

The catalyst component for addition polymerization of the present invention is a catalyst component for addition polymerization composed of a transition metal compound of the general formula [1], and catalysts for addition polymerization having a high activity are obtained by contacting this component with a co-catalyst component for activation.

The co-catalyst component for activation is preferably the following (B) and/or (C), and the catalyst for addition polymerization of the present invention is preferably a catalyst for addition polymerization obtained by bringing a transition metal compound (A) of the general formula [1] into contact with an organoaluminum compound selected from the group consisting of the following (B1), and at least one aluminoxane selected from the group consisting of the following (B2) and (B3) and/or a boron compound selected from the group consisting of the following (C), or with at least one aluminoxane selected from the group consisting of the following (B2) and (B3) and/or a boron compound selected from the group consisting of the following (C):

(B1) organic aluminum compounds of the general formula $E^1{}_aAlZ_{3-a}$, (B2) cyclic aluminoxanes having a structure of the general formula $\{-Al(E^2)-O-\}_b$, (B3) linear aluminoxanes having a structure of the general formula $E^3\{-Al(E^3)-O-\}_cAlE^3{}_2$ (wherein, each of $E^1$, $E^2$ and $E^3$ represents a hydrocarbon group, and all $E^1$s, all $E^2$s or all $E^3$s may be the same or different. Z represents a hydrogen atom or halogen atom, and all Zs may be the same or different. a represents a number satisfying $0 < a \leq 3$, b represents an integer of 2 or more, and c represent an integer of 1 or more.), (C) one or more boron compounds selected from the following (Cl) to (C3):

(C1) boron compounds represented by the general formula $BQ^1Q^2Q^3$, (C2) boron compounds represented by the general formula $G^+(BQ^1Q^2Q^3Q^4)^-$, (C3) boron compounds represented by the general formula $(L-H)^+(BQ^1Q^2Q^3Q^4)^-$ (wherein, B represents a trivalent boron atom in valance state, and $Q^1$ to $Q^4$ represent a halogen atom, hydrocarbon group, halogenated hydrocarbon group, substituted silyl group, alkoxy group or di-substituted amino group, and they may be the same or different. $G^+$ represents an inorganic or organic cation, and L represents a neutral Lewis base and $(L-H)^+$ represents a Brønsted acid.).

The catalyst for addition polymerization will be further illustrated in detail below.

(B) Aluminum Compound

The aluminum compound (B) includes organoaluminum compounds of the following (B1) and aluminoxanes of the following(B2) and (B3).

(B1) organic aluminum compounds represented by the general formula $E^1{}_aAlZ_{3-a}$, (B2) cyclic aluminoxanes having a structure represented by the general formula $\{-Al(E^2)-O-\}_b$.

(B3) linear aluminoxanes having a structure represented by the general formula $E^3\{-Al(E^3)-O-\}_cAlE^3{}_2$ (wherein, each of $E^1$, $E^2$ and $E^3$ represents a hydrocarbon group; all $E^1$s, all $E^2$s or all $E^3$ s maybe the same or different; Z represents a hydrogen atom or halogen atom; all Zs may be the same or different; a represents a number satisfying $0<a<3$; b represents an integer of 2 or more; and c represent an integer of 1 or more.).

As the hydrocarbon group represented by $E^1$, $E^2$ and $E^3$, a hydrocarbon group having 1 to 8 carbon atoms is preferable, and an alkyl group is more preferable.

Specific examples of the organic aluminum compound (B1) represented by the general formula $E^1{}_aAlZ_{3-a}$ include trialkylaluminums such as trimethylaluminum, triethylaluminum, tripropylaluminum, triisobutylaluminum, trihexylaluminum and the like; dialkylaluminum chlorides such as dimethylaluminum chloride, diethylaluminumchloride, dipropylaluminumchloride, diisobutylaluminum chloride, dihexylaluminum chloride and the like; alkylaluminum dichlorides such as methylaluminum dichloride, ethylaluminum dichloride, propylaluminum dichloride, isobutylaluminum dichloride, hexylaluminum dichloride and the like; dialkylaluminum hydrides such as dimethylaluminum hydride, diethylaluminum hydride, dipropylaluminum hydride, diisobutylaluminum hydride, dihexylaluminum hydride and the like, etc.

Trialkylaluminums are preferable, and triethylaluminum or triisobutylaluminum is more preferable.

As specific examples of $E^2$ and $E^3$ in cyclic aluminoxanes (B2) having a structure of the general formula $\{-Al(E^2)-O-\}_b$, and linear aluminoxanes (B3) having a structure of the general formula $E^3\{-Al(E^3)-O-\}_cAlE^3{}_2$, alkyl groups such as a methyl group, ethyl group, n-propyl group, isopropyl group, n-butyl group, isobutyl group, n-pentyl group, neopentyl group and the like can be exemplified. b in an integer of 2 or more, and c is an integer of 1 or more. Preferably, $E^2$ and $E^3$ are a methyl group or isobutyl group, n is 2 to 40, and c is 1 to 40.

The above-mentioned aluminoxane is produced by various methods. The method is not particularly restricted, and it may be advantageously carried out according to a known method. For example, a trialkylaluminum (for example, trimethylaluminum and the like) is dissolved in a suitable organic solvent (benzene, aliphatic hydrocarbon and the like) to prepare a solution which is allowed to contact with water. Alternatively, there is exemplified a method in which a trialkylaluminum (for example, trimethylaluminum and the like) is allowed to contact with a metal salt containing crystal water (for example, copper sulfate hydrate and the like).

The aluminoxane produced by such methods is usually supposed to be a mixtures of a cyclic aluminoxane and a linear aluminoxane.

(C) Boron compound

As the boron compound (C), one or more boron compounds selected from (Cl) boron compounds represented by the general formula $BQ^1Q^2Q^3$, (C2) boron compounds represented by the general formula $G^+(BQ^1Q^2Q^3Q^4)$, and (C3) boron compounds represented by the general formula $(L-H)^+(BQ^1Q^2Q^3Q^4)$ are used, in the present invention.

In the boron compound (Cl) of the general formula $BQ^1Q^2Q^3$, B represents a trivalent boron atom, and $Q^1$ to $Q^3$ represent a halogen atom, hydrocarbon group, halogenated hydrocarbon group, substituted silyl group, alkoxy group or di-substituted amino group, and they may be the same or different. $Q^1$ to $Q^3$ preferably represent a halogen atom, a hydrocarbon group having 1 to 20 carbon atoms, a halogenated hydrocarbon group having 1 to 20 carbon atoms, a substituted silyl group having 1 to 20 carbon atoms, an alkoxy group having 1 to 20 carbon atoms, or an amino group having 1 to 20 carbon atoms, and $Q^1$ to $Q^3$ more preferably represent a halogen atom, a hydrocarbon group having 1 to 20 carbon atoms or a halogenated hydrocarbon group having 1 to 20 carbon atoms. Further preferably, $Q^1$ to $Q^4$ represent a fluorinated hydrocarbon group having 1 to 20 carbon atoms containing at least one fluorine atom, and particularly preferably, $Q^1$ to $Q^4$ represent a fluorinated aryl group having 6 to 20 carbon atoms containing at least fluorine atom.

Specific examples of the compound (C1) include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis (pentafluorophenyl)borane and the like, and tris(pentafluorophenyl)borane is most preferable.

In the boron compound (C2) of the general formula $G^+(BQ^1Q^2Q^3Q^4)$, $G^+$ represents an inorganic or organic cation, B represents a trivalent boron atom, and $Q^1$ to $Q^4$ are as defined for $Q^1$ to $Q^3$ in the above-mentioned (C1).

As specific examples of an inorganic cation G+in the compound of the general formula $G^+(BQ^1Q^2Q^3Q^4)^-$, a ferrocenium cation, alkyl-substituted ferrocenium cation, silver cation and the like are listed, and as specific examples of an organic cation $G^+$ in the compound, a triphenylmethyl cation and the like are listed. $G^+$ represents preferably a carbenium cation, and particularly preferably a triphenylmethyl cation. As $(BQ^1Q^2Q^3Q^4)^-$, there are listed tetrakis(pentafluorophenyl)borate, tetrakis(2,3,5,6-tetrafluorопhеny)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluorophenyl)borate, tetrakis(3,5-bistrifluoromethylphenyl)borate and the like.

As specific combinations thereof, ferrocenium tetrakis(pentafluorophenyl)borate, 1,1'-dimethylferrocenium tetrakis(pentafluorophenyl)borate, silver tetrakis(pentafluorophenyl)borate, tripheylmethyltetrakis(pentafluorophenyl)borate, triphenylmethyltetrakis(3,5-bistrifluoromethylphenyl)borate, and the like are listed, and triphenylmethyltetrakis(pentafluorophenyl)borate is most preferable.

In the boron compound (C3) of the general formula $(L-H)^+(BQ^1Q^2Q^3Q^4)$, L represents a neutral Lewis base and $(L-H)^+$ represents a Brønsted acid, B represents a trivalent boron atom, and $Q^1$ to $Q^4$ are as defined for $Q^1$ to $Q^3$ in the above-mentioned Lewis acid (C1).

As specific examples of the Brønsted acid (L-H)+in the compound of the general formula $(L-H)+(BQ^1Q^2Q^3Q^4)^-$, trialkyl-substituted ammoniums, N,N-dialkylaniliniums, dialkylammoniums, triarylphosphoniums and the like are listed, and as $(BQ^1Q^2Q^3Q^4)^-$, the same moieties as described above are listed.

As specific combinations thereof, triethylammoniumtetrakis(pentafluorophenyl)borate, tripropylammonium tetrakis(pentafluorophenyl)borate, tri(n-butyl)ammoniumtetrakis(pentafluorophenyl)borate, tri(n-butyl)ammonium tetrakis(3,5-bistrifluoromethylphenyl)borate, N,N-dimethylaniliniumtetrakis(pentafluorophenyl)borate, N,N-diethylanilinium tetrakis(pentafluorophenyl)borate, N,N-2,4,6-pentamethylaniliniumtetrakis(pentafluorophenyl)borate, N,N-dimethylaniliniumtetrakis(3,5-bistrifluoromethylphenyl)borate, diisopropylammoniumtetrakis(pentafluorophenyl)borate, dicyclohexyammoniumtetrakis(pentafluorophenyl)borate, triphenylphosphoniumtetrakis(pentafluorophenyl)borate, tri(methylphenyl)phosphoniumtetrakis(pentafluorophenyl)borate, tri(dimethylphenyl)phosphoniumtetrakis(pentafluorophenyl)borate and the like are listed, and most preferable is tri(n-butyl)ammonium tetrakis(pentafluorophenyl)borate, or N,N-dimethylaniliniumtetrakis(pentafluorophenyl)borate.

[Production of addition polymer]

The process for producing an addition polymer of the present invention is a process for producing an addition polymer comprising polymerizing an addition polymerizable monomer with the above-mentioned catalyst for addition polymerization.

Contact in producing a catalyst for addition polymerization by bringing the above-mentioned transition metal compound into contact with a co-catalyst component for activation (components (B1)-(B3), and (C)) may be conducted by any means providing the transition metal compound and the co-catalyst for activation are in contact to form a catalyst, and there are adopted a method in which a transition metal compound and a co-catalyst for activation are previously diluted by a solvent or not diluted, before they are mixed for mutual contact, and a method in which a transition metal compound and a co-catalyst for activation are separately fed into a polymerization reactor for mutual contact thereof. As the co-catalyst for activation, a plurality of compounds may be combined and used, however, it is needless to say that a part of which may be previously mixed and used, or they may be separately fed into a polymerization reactor and used.

It is desirable to use components so that the molar ratio of (B)/transition metal compound (A) is from 0.1 to 10000, preferably from 5 to 2000, and the molar ratio of (C)/transition metal compound (A) is from 0.01 to 100, preferably from 0.5 to 10.

The concentrations of components when they are used in the form of a solution, or suspension or slurry in a solvent are appropriately selected depending on the ability of an apparatus for feeding components into a polymerization reactor, and it is generally desirable that the concentration of the transition metal compound (A) is usually from 0.001 to 200 mmol/L, more preferably from 0.01 to 100 mmol/L, further preferably from 0.05 to 50 mmol/L, the concentration of (B) is, in terms of an Al atom, usually from 0.01 to 5000 mmol/L, more preferably from 0.1 to 2500 mmol/L, further preferably 0.1 to 2000 mmol/L, and the concentration of (C) is usually from 0.001 to 500 mmol/L, more preferably from 0.01 to 250 mmol/L, further preferably from 0.05 to 100 mmol/L.

The process for producing an addition polymer of the present invention can be applied to various polymerization methods of addition polymerizable monomers, and of them, is suitable as a process for producing a polymer of an olefin and/or alkenyl aromatic hydrocarbon.

As the olefins herein referred to, olefins having 2 to 20 carbon atoms, particularly, ethylene, α-olefins having 3 to 20 carbon atoms, diolefins having 4 to 20 carbon atoms, and the like can be used, and two or more olefins can be used simultaneously. Specific examples of the olefin include, for example, linear olefins such as ethylene, propylene, 1-butene, 1-pentene, 1-hexene, 1-heptene, 1-octene, 1-nonene, 1-decene and the like, branched olefins such as 3-methyl-1-butene, 3-methyl-1-pentene, 4-methyl-1-pentene, 5-methyl-1-hexene and the like, vinylcyclohexane, and the like. Specific examples of combinations of monomers in conducting copolymerization, include, for example, ethylene and propylene, ethylene and 1-butene, ethylene and 1-hexene, ethylene and 1-octane, propylene and 1-butene, and the like.

As the above-mentioned alkenyl aromatic hydrocarbon, alkenyl aromatic hydrocarbons having an aromatic hydrocarbon group of 6 to 25 carbon atoms are preferable, and specific examples thereof include, for example, a phenyl group, tolyl group, xylyl group, tert-butylphenyl group, vinylphenyl group, naphthyl group, phenanethryl group, anthracenyl group and the like. The aromatic hydrocarbon group is preferably a phenyl group, tolyl group, xylyl group, tert-butylphenyl group, vinylphenyl group ornaphthylgroup. Examples of thealkenylaromatichydrocarbon include alkylstyrenes such as p-methylstyrene, m-methylstyrene, o-methylstyrene, p-ethylstyrene, m-ethylstyrene, o-ethylstyrene, 2,4-dimethylstyrene, 2,5-dimethylstyrene, 3,4-dimethylstyrene, 3,5-dimethylstyrene, 3-methyl-5-ethylstyrene, p-tert-butylstyrene, p-sec-butylstyrene and the like; alkenylbenzenes such as styrene, 2-phenylpropylene, 2-phenylbutene and the like; and vinylnaphthalenes such as 1-vinylnaphthalene and the like. Among them, styrene, p-methylstyrene, m-methylstyrene, o-methylstyrene, p-tert-butylstyrene, 2-phenypropylene and 1-vinylnaphthalene are preferred, and styrene is particularly preferred.

The process for producing an addition polymer of the present invention is suitable for producing a copolymer of the above-mentioned olefin with the above-mentioned alkenyl aromatic hydrocarbon, and as the combination of monomers in this process, combinations of ethylene and styrene, propylene and styrene, ethylene, propylene and styrene are listed, and particularly, this process is suitable for producing a copolymer of ethylene with styrene.

The process for producing an addition polymer of the present invention is particularly suitable for producing copolymers of ethylene and α-olefins having 3 to 8 carbon atoms, particularly, linear low density polyethylenes.

The polymerization method should also not be limited particularly, and for example, solvent polymerization using, as a solvent, an aliphatic hydrocarbon such as butane, pentane, hexane, heptane, octane or the like, an aromatic hydrocarbon such as benzene, toluene or the like, or a halogenatedhydrocarbon such as methylene dichloride or the like, or slurry polymerization, gas phase polymerization in gaseous monomer(s), and the like can be applied, and any of continuous polymerization and batch-wise polymerization is possible.

The polymerization temperature can be usually from −50° C. to 200° C., and is particularly, preferably from −20° C. to 100° C., and the polymerization pressure is usually preferably from normal pressure to 60 kg/cm². The polymerization time is generally determined appropriately depending on the kind of the intended polymer, and the reaction apparatus, and usually, it can be from 1 minute to 20 hours. Further, in the present invention, a chain transfer agent such as hydrogen or the like can also be added for controlling the molecular weight of a copolymer.

EXAMPLE

The present invention is illustrated using the following Examples and Comparative Examples in more detail below, but not limited thereto.

The properties of polymers in Examples were measured by the following methods.
(1) Intrinsic viscosity [η] was measured by using a Ubbellohde viscometer in a tetralin solution at 135° C.
(2) Weight-average molecular weight (Mw), number-average molecular weight (Mn) and molecular weight distribution (Mw/Mn): The molecular weights were measured by gel permeation chromatography (GPC) under the following conditions. A calibration curve was made by using standard polystyrene. The molecular weight distribution was evaluated as a ratio (Mw/Mn) of the weight-average molecular weight (Mw) to the number-average molecular weight (Mn).

| | |
|---|---|
| Machine | 150CV type, manufactured by Millipore Waters |
| Column | Shodex M/S 80 |
| Measurement temperature | 145° C., solvent: orthodichlorobenzene |
| Sample concentration | 5 mg/8 ml |

(3) Content of repeating units derived from α-olefin in ethylene-α-olefin copolymer (α-olefin content):
It was measured from the specific absorptions of ethylene and α-olefin using an infrared spectrophotometer (IR-810, manufactured by Nippon Bunko Kogyo K.K.), and represented in terms of short chain branch (SCB) numbers per 1000 carbons.
(4) Melting Point of Copolymer:
(In the case of Example 9)
It was measured by using Seiko SSC-5200 under the following conditions.

Cooling: 20° C. to −50° C. (20° C./min.), kept for 5 minutes
Heating: −50° C. to 20° C. (20° C./min.), kept for 5 minutes
Cooling: 20° C. to −5° C. (20° C./min.), kept for 5 minutes
Measurement: −50° C. to 300° C. (20° C./min.)
(In other case than Example 9)
It was measured by using Seiko SSC-5200 under the following conditions.
Heating: 40° C. to 100° C. (10° C./min.), kept for 5 minutes
Cooling: 150° C. to 10° C. (5° C./min.), kept for 10 minutes
Measurement: 10° C. to 160° C. (5° C./min.)

EXAMPLE 1(1)

Synthesis of [chlorotetrakis(dimethylphenylphosphine) tungsten] (μ-dinitrogen) [dichloro(cyclopentadienyl) titanium]

225.2 mg (0.284 mmol) of cis-bis(dinitrogen)tetrakis (dimethylphenylphosphine)tungsten and 62.2 mg (0.284 mmol) of trichloro(cyclopentadienyl)titanium were dissolved in 5 ml of benzene, to recognize generation of a gas from the solution, and the color of the solution changed from orange to dark green. This solution was stirred for 8 hours, then, the solvent was distilled off to obtain dark green solid. The dark green solid was subjected to extraction with methylene chloride, and the resulted extracted substance was re-crystallized by using a methylene chloride/ether mixed solvent, to obtain 196.0 mg of a black crystal. Yield: 70%.

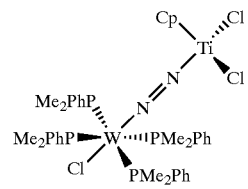

$^1$H-NMR(CDCl$_3$) δ:1.63 (s, 24H, PMe),6.44 (s, 5H, Cp), 7.27–7.46 (m, 20H, Ph);

$^{31}$P($^1$H)-NMR(CDCl$_3$) δ: −24.5 (s with $^{183}$W satellites, J$_{WP}$=277 Hz);

IR(KBr) 1408(m)cm$^{-1}$.

Anal. Calcd. for C$_{37}$H$_{49}$Cl$_3$N$_2$P$_4$TiW: C, 45.17; H, 5.02; N, 2.85. Found: C, 45.50; H, 5.29; N, 2.70

EXAMPLE 1(2)

Synthesis of {chlorobis[1,2-bis(diphenylphosphino) ethane]tungsten}(μ-dinitrogen)[dichloro(cyclopentadienyl) titanium] (diethyl ether) (dichloromethane);

198.0 mg (0.191 mmol) of trans-bis(N$_2$)bis [1,2-bis (diphenylphosphino)ethane]tungsten and 41.9 mg (0.191 mmol) of trichloro(cyclopentadienyl) titanium were dissolved in 5 ml of tetrahydrofuran under room temperature, to recognize generation of a gas from the solution, and the color of this solution changed from orange to dark green. This solution was stirred for 8 hours, then, the solvent was distilled off to obtain dark green solid. The dark green solid was subjected to extraction with methylene chloride, and the resulted extracted substance was re-crystallized by using a methylene chloride/ether mixed solvent, to obtain 166.2 mg of a black crystal. Yield: 63%.

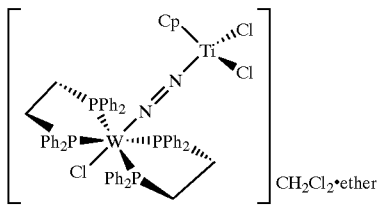

$^1$H NMR (CDCl$_3$) δ:1.21 (s, 6H, J=6.8 Hz, Me of ether), 2.46, 2.89 (br, 4H, each, CH$_2$ of dppe), 3.48 (q, 4H, J=7.3 Hz, CH$_2$ of ether), 5.29 (s, 2H, CH$_2$Cl$_2$), 5.70(s, 5H, Cp), 6.66–7.67(m, 40H, Ph);

$^{31}$P{$^1$H} NMR (CDCl$_3$) δ:36.0 (s with $^{183}$W satellites, JWP=284 Hz);

IR (KBr) 1412(m) cm$^{-1}$.

Anal. Calcd for C$_{63}$H$_{65}$Cl$_5$N$_2$OP$_4$TiW: C, 53.69; H, 4.72; N, 2.02. Found: C, 53.49; H, 4.60; N, 2.19

EXAMPLE 1(3)

Synthesis of {chlorobis[1,2-bis(diphenylphosphino)ethane] molybdenum}(μ-dinitrogen) [dichloro (cyclopentadienyl)titanium];

194.7 mg (0.205 mmol) of trans-bis(dinitrogen)bis[1,2-bis (diphenylphosphino)ethane]molybdenum and 45.0 mg (0.205 mmol) of trichloro(cyclopentadienyl)titanium were dissolved in 5 ml of tetrahydrofuran under room temperature, to recognize generation of a gas from the solution, and the color of this gas changed from orange to dark green. This solution was stirred for 8 hours, then, the solvent was distilled off to obtain dark green solid. The dark green solid was subjected to extraction with methylene chloride, and the resulted extracted substance was re-crystallized by using a methylene chloride/ether mixed solvent, to obtain 182.3 mg of a black crystal. Yield: 78%.

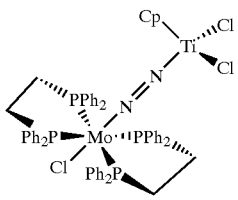

$^1$H-NMR(CDCl$_3$) δ:2.31, 2.66 (br, 4H each, CH$_2$ of dppe), 5.73 (s, 5H, Cp), 6.78–7.77 (m, 40H, Ph);
$^{31}$P{$^1$H}NMR(CDCl$^3$) δ:52.9 (s);
IR(KBr) 1416(m)cm$^{-1}$.

Anal. Calcd for C$_{57}$H$_{53}$Cl$_3$MoN$_2$P$_4$Ti: C, 60.05; H, 4.69; N, 2.46. Found: C, 60.13; H, 5.06; N, 2.22

EXAMPLE 1(4)

Synthesis of {chlorobis[1,2-bis(diphenylphosphino)ethane]tungsten}(μ-dinitrogen)[trichloro (cyclopentadienyl)niobium](diethylether);

164.6 mg (0.159 mmol) of trans-bis(dinitrogen)bis [1,2-bis(diphenylphosphino)ethane]tungsten and 47.6 mg (0.159 mmol) of tetrachloro(cyclopentadienyl)niobium were dissolved in 5 ml of tetrahydrofuran under room temperature, to recognize generation of a gas from the solution, and the color of this gas changed from orange to black. This solution was stirred for 1 hour, then, the solvent was distilled off to obtain dark green solid. The dark green solid was subjected to extraction with methylene chloride, and the resulted extracted substance was re-crystallized by using a methylene chloride/ether mixed solvent, to obtain 164.8 mg of a black crystal. Yield: 75%.

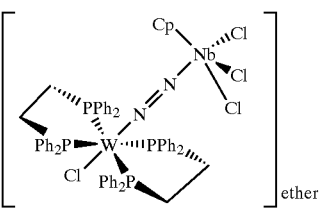

$^1$H-NMR(CDCl$_3$) δ:1.12 (t, 6H, J=7.0 Hz, Me of ether), 2.68, 2.90 (br, 4H each, CH$_2$ of dppe), 3.38 (t, 4H, J=7.2 Hz, CH$_2$ of ether), 5.86 (s, 5H, Cp), 6.67–7.66 (m, 40H, Ph);

$^{31}$P($^1$H)-NMR(CDCl$_3$) δ:34.1 (s with $^{183}$W satellites, J$_{WP}$=275 Hz);

IR(KBr)1383(m)cm$^{-1}$.

Anal. Calcd for C$_{61}$H$_{63}$Cl$_4$N$_2$NbOP$_4$W: C, 52.99; H, 4.59; N, 2.03. Found:C, 52.88; H, 4.22; N, 2.32

EXAMPLE 1(5)

Synthesis of {chlorobis[1,2-bis(diethylphosphino)ethane]tungsten}(μ-dinitrogen) [dichloro(cyclopentadienyl) titanium];

326 mg (0.50 mmol) of trans-bis(dinitrogen)bis[1,2-bis (diethylphosphino)ethane]tungsten and 110 mg (0.50 mmol) of trichloro(cyclopentadienyl)titanium were dissolved in 7.5 ml of tetrahydrofuran under room temperature, and the mixture was stirred for 21 hours. The solvent was distilled off from the resulted violet black solution and the resultant solution was subjected to extraction with 8 ml of dichloromethane, then, the resulted extracted solution was concentrated to 1.5 ml. To this was added slowly 8.5 ml of hexane, to obtain 320 mg of a black crystal. Yield: 76%.

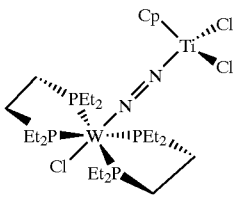

$^1$H-NMR(CDCl$_3$) δ:6.17 (s, 5H, C$_5$H$_5$), 2.18–1.76 (m, 24H, PCH2), 1.29–1.13 (m, 24H, PCH2CH3);
$^{31}$P{$^1$H}-NMR(CDCl$_3$) δ:30.99 (s with 183W satellites, J(PW)=270 Hz);
IR(KBr) 1406.3(s)cm$^{-1}$.

Anal. Calcd. for C$_{25}$H$_{53}$Cl$_3$N2P4TiW: C, 35.59; H, 6.33; N, 3.32. Found: C, 35.50; H, 6.44; N, 3.50.

EXAMPLE 1(6)

Synthesis of {chlorobis[1,2-bis(diethylphosphino)ethane] tungsten}(μ-dinitrogen) [dichloro (pentamethylcyclopentadienyl) titanium];

0.50 mg (0.77 mmol) of trans-bis(dinitrogen)bis[1,2-bis (diethylphosphino)ethane]tungsten and 0.22 g (0.76 mmol)

of trichloro(pentamethylcyclopentadienyl)titanium were dissolved in 15 ml of tetrahydrofuran under room temperature, and the mixture was stirred for 15 hours. In this procedure, foaming was caused by gas generation from the red solution, and it changed to dark green suspension. The solvent was distilled off from this suspension and the suspension was subjected to extraction with 10 ml of dichloromethane, then, the resulted extracted solution was concentrated, and to this was added slowly diethyl ether to cause re-crystallization giving 0.48 g of a dark green crystal. Yield: 68%.

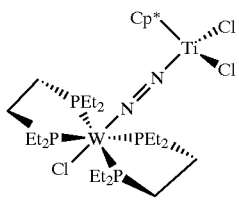

$^1$H-NMR(CDCl$_3$) δ:2.22-1.70 (m, 24H, PCH2), 1.97 (s, 15H, Cp-CH3), 1.30–1.10 (m, 24H, PCH2CH3); IR(KBr) 1406.5(s)cm$^{-1}$.

EXAMPLE 1(7)

Synthesis of {chlorobis[1,2-bis(diethylphosphino)ethane]tungsten}(μ-dinitrogen) [dichloro(indenyl)titanium];

0.252 mg (0.387 mmol) of trans-bis(dinitrogen)bis [1,2-bis(diethylphosphino)ethane]tungsten and 0.105 g (0.390 mmol) of trichloro(indenyl)titanium were dissolved in 10 ml of tetrahydrofuran under room temperature, and the mixture was stirred for 22 hours. In this procedure, foaming was caused by gas generation from the red solution, and it changed to dark green suspension. The solvent was distilled off from this suspension and the resulted solid was subjected to extraction with 9 ml of dichloromethane, then, the resulted extracted solution was concentrated, and to this was added slowly diethyl ether to cause re-crystallization giving 0.25 g of a dark green crystal. Yield: 72%.

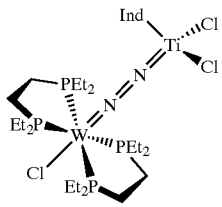

$^1$H-NMR(CDCl$_3$) δ:7.34(s, 2H, Ind), 6.98(s, 2H, Ind), 6.62(s, 1H, Ind), 6.17(s, 2H, Ind), 2.18–1.60(m, 24H, P—CH$_2$), 1.26–1.03(m, 24H, CH$_3$—CH$_2$).

EXAMPLE 1(8)

Synthesis of (chlorobis[1,2-bis(diphenylphosphino)ethane]tungsten}(μ-dinitrogen) [dichloro(pentamethylcyclopentadienyl) titanium];

480 mg (0.46 mmol) of trans-bis(dinitrogen)bis [1,2-bis(diphenylphosphino)ethane]tungsten and 140 mg (0.48 mmol) of trichloro(pentamethylcyclopentadienyl)titanium were dissolved in 25 ml of tetrahydrofuran under room temperature, to recognize generation of a gas from the solution, and the color of this solution changed from red to dark green. This solution was stirred for 18 hours, then, the solvent was distilled off to obtain dark green solid. The dark green solid was subjected to extraction with methylene chloride, and the resulted extracted substance was re-crystallized by using a methylene chloride/ether mixed solvent, to obtain 490 mg of a dark green fine crystal. Yield: 82%.

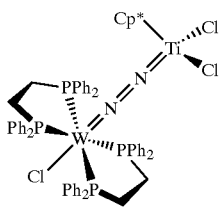

$^1$H-NMR(CDCl$_3$) δ:1.72 (s, 15H, Cp-CH$_3$),2.36, 2.87 (m, 4H, each, CH$_2$ of dppe), 6.57 (m, 8H, Ph), 6.89 (t, 8H, Ph), 7.09 (t, 4H, Ph), 7.38 (t, 4H, Ph), 7.45 (t, 8H, Ph), 7.76 (m, 8H, Ph);

$^{31}$P{$^1$H} NMR (CDCl$_3$) δ: 38.7 (s with $^{183}$W satellites, J$_{WP}$=287 Hz);

IR(KBr) 1409(m)cm$^{-1}$.

Anal. Calcd for C$_{63}$H$_{65}$Cl$_5$N$_2$OP$_4$TiW: C, 57.36; H, 4.89; N, 2.16. Found: C, 57.06; H, 5.16; N, 2.17

EXAMPLE 1(9)

Synthesis of {bis[1,2-bis(diphenylphosphino)ethane](isothiocyanide) tungusten} (μ-dinitrogen) [dichloro(cyclopentadienyl)titanium](3.dichloromethane);

109.7 mg (0.084 mmol) of(tetra-n-butylammonium) [trans-(dinitrogen)bis[1,2-bis(diphenylphosphino)ethane]tungusten and 18.4 mg (0.084 mmol) of trichloro(cyclopentadienyl)titanium were dissolved in 3 ml of benzene under room temperature, and the solution was stirred for 17 hours, then, the solvent was distilled off to obtain a green solid. The green solid was subjected to extraction with methylene chloride, and the resulted extracted substance was re-crystallized by using a methylene chloride/ether mixed solvent, to obtain 68.0 mg of a dark green crystal. Yield: 54%.

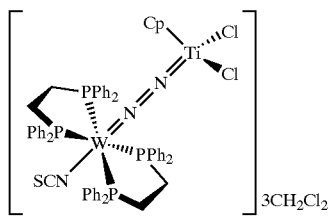

$^1$H-NMR(CDCl$_3$) δ:1.72 (s, 15H, Cp-CH$_3$), 2.49, 2.81 (m, 4H, each, CH$_2$ of dppe), 5.80 (s, 5H, Cp), 6.55–7.63 (m, 40H, Ph);

$^{31}$P{$^1$H) NMR (CDCl$_3$) δ: 38.2 (s with $^{183}$W satellites, J$_{WP}$=284 Hz); IR(KBr) 1441 (m)cm$^{-1}$.

Anal. Calcd for C$_{63}$H$_{65}$Cl$_5$N$_2$ OP$_4$ TiW: C, 48.67; H, 3.95; N, 2.79.

Found: C, 49.02; H, 3.77; N, 2.88.

EXAMPLE 1(10)

Synthesis of {chlorobis[1,2-bis(diphenylphosphino) ethane] tungusten}(μ-dinitrogen) [dichloro (methylcyclopentadienyl) titanium];

500 mg (0.48 mmol) of [trans-bis(dinitrogen)bis [1,2-bis (diphenylphosphino)ethane]tungusten and 110 mg (0.48 mmol) of trichloro(methylcyclopentadienyl)titanium were dissolved in 25 ml of tetrahydrofuran under room temperature, to recognize generation of a gas from the solution, and the color of this solution changed from orange to dark brown. The solution was stirred for 24 hours, then, the solvent was distilled off to obtain a black solid. The black solid was subjected to extraction with methylene chloride, and the resulted extracted substance was re-crystallized by using a methylene chloride/ether mixed solvent, to obtain 540 mg of a bright black cubic crystal. Yield: 90%.

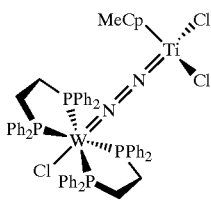

$^1$H-NMR(toluene-$d_8$) δ:2.00 (s, 3H, Cp-CH$_3$), 2.39, 2.81 (m, 4H, each, CH$_2$ of dppe), 5.27, 5.47 (t, 2H, each, Cp-H), 6.59 (s, 8H, Ph), 6.87 (m, 8H, Ph), 7.04 (m, 4H, Ph), 7.30 (m, 12H, Ph), 7.60 (s, 8H, Ph);

$^{31}$P{$^1$H}-NMR(CD$_2$Cl$_2$) δ:39.9 (s with $^{183}$W satellites, J$_{WP}$=286 Hz); IR(KBr) 1411(m)cm$^{-1}$.

Anal. Calcd. for C$_{63}$H$_{65}$Cl$_5$N$_2$OP$_4$TiW: C, 56.09; H, 4.46; N, 2.26. Found: C, 56.02; H, 4.56; N, 2.21.

EXAMPLE 1(11)

Synthesis of (chlorobis[1,2-bis(diethylphosphino) ethane] tungusten}(μ-dinitrogen) [dichloro (methylcyclopentadienyl) titanium];

260 mg (0.40 mmol) of [trans-bis(dinitrogen)bis [1,2-bis (diethylphosphino)ethane]tungusten and 90 mg (0.39 mmol) of trichloro(methylcyclopentadienyl)titanium were dissolved in 15 ml of tetrahydrofuran under room temperature, to recognize generation of a gas from the solution, and the color of this solution changed from orange to dark brown. The solution was stirred for 14 hours, then, the solvent was distilled off to obtain a black solid. The black solid was subjected to extraction with methylene chloride, and the resulted extracted substance was re-crystallized by using a methylene chloride/ether mixed solvent, to obtain 308 mg of a dark blue needle-like crystal. Yield: 92%.

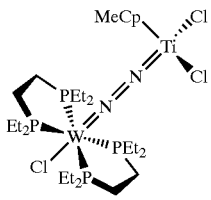

$^1$H-NMR(toluene-$d_8$) δ:0.93, 1.15 (m, 4H, each, CH$_2$ of depe), 1.68, 1.85 (m, 4H, each, CH$_2$ of depe), 1.41, 1.97 (m, 8H, each, CH$_2$ of depe), 2.27 (s, 3H, Cp-CH$_3$), 5.82, 6.01 (t, 2H, each, Cp-H);

$^{31}$P{$^1$H}-NMR(CD$_2$Cl$_2$) δ:36.0 (s with $^{183}$W satellites, J$_{WP}$=269 Hz);
IR(KBr) 1407(m)cm$^{-1}$.

Anal. Calcd. for C$_{63}$H$_{65}$Cl$_5$N$_2$OP$_4$TiW: C, 36.41; H, 6.46; N, 3.27. Found: C, 36.82; H, 6.69; N, 3.21.

EXAMPLE 2

An autoclave reactor having an inner volume of 0.4 liter equipped with a stirrer was dried under vacuum and purged with argon, then, 200 ml of toluene as a solvent was charged into this, and the reactor was heated up to 60° C. After heating, ethylene was fed while controlling the ethylene pressure at 0.6 MPa, and after the system was stabilized, 0.50 mmol (mol number in terms of aluminum atom; hereinafter the same) of a solution of methylisobutylaluminoxane in toluene (MMAO3A manufactured by Tosoh Akzo Ltd.; hereinafter, abbreviated simply as MMAO" was charged, and subsequently, 0.1 μmol of [chlorotetrakis (dimethylphenylphosphine)tungsten](μ-dinitrogen) [dichloro(cyclopentadienyl)titanium] synthesized in the above-mentioned Example 1(1) was charged. Polymerization was conducted for 60 minutes while controlling the temperature at 60° C.

As a result of polymerization, an ethylene polymer having a melting point of 136.7° C. was produced at a rate of 2.3×10$^7$ g per one hour per 1 mol of a titanium atom.

EXAMPLE 3

An autoclave reactor having an inner volume of 0.4 liter equipped with a stirrer was dried under vacuum and purged with argon, then, 200 ml of toluene as a solvent was charged into this, and the reactor was heated up to 60° C. After heating, ethylene was fed while controlling the ethylene pressure at 0.6 MPa, and after the system was stabilized, 0.25 mmol of triisobutylaluminum was charged, subsequently, 0.1 μmol of [chlorotetrakis (dimethylphenylphosphine)tungsten](μ-dinitrogen) [dichloro(cyclopentadienyl)titanium] was charged, and subsequently, 1.0 μmol of triphenylmethyltetrakis (pentafluorophenyl)borate (called as "[triphenylcarbenium] [tetrakis(pentafluorophenyl)borate]) was charged. Polymerization was conducted for 60 minutes while controlling the temperature at 60° C.

As a result of polymerization, an ethylene polymer having a melting point of 136.8° C. was produced at a rate of 1.8×10$^7$ g per one hour per 1 mol of a titanium atom.

EXAMPLE 4

An autoclave reactor having an inner volume of 0.4 liter equipped with a stirrer was dried under vacuum and purged with argon, then, 198 ml of toluene as a solvent was charged into this, 2 ml of 1-hexene as an α-olefin was charged, and the reaction vessel was heated up to 60° C. After temperature raise, ethylene was fed while controlling the ethylene pressure at 0.6 MPa, and after the system was stabilized, 0.05 mmol of MMAO was charged, and subsequently, 0.5 μmol of {chlorobis[1,2-bis(diphenylphosphino)ethane] molybdenum}(μ-dinitrogen) [dichloro(cyclopentadienyl) titanium] synthesized in the above-mentioned Example 1(3) was charged. Polymerization was conducted for 60 minutes while controlling the temperature at 60° C.

As a result of polymerization, a copolymer of ethylene and 1-hexene having a SCB of 18.3, [η] of 4.9 dl/g, a Mw of 3.5×10$^5$, a Mw/Mn of 2.14 and melting points of 92.0° C. and 119.6C was produced at a rate of 1.7×10$^7$ g per one hour per 1 mol of a titanium atom.

COMPARATIVE EXAMPLE 1

An autoclave reactor having an inner volume of 0.4 liter equipped with a stirrer was dried under vacuum and purged with argon, then, 198 ml of toluene as a solvent was charged into this, 2 ml of 1-hexeneas an α-olefin was charged, and the reaction vessel was heated up to 60° C. After temperature raise, ethylene was fed while controlling the ethylene pressure at 0.6 MPa, and after the system was stabilized, 0.05 mmol of MMAO was charged, and subsequently, 0.5 μmol of (cyclopentadienyl)titanium trichloride was charged. Polymerization was conducted for 60 minutes while controlling the temperature at 60° C.

As a result of polymerization, a copolymer of ethylene and 1-hexene having a SCB of 18.6, a Mw of $2.3 \times 10^5$, a Mw/Mn of 2.43 and melting points of 99.0° C. and 115.6C was produced at a rate of $1.6 \times 10^7$ g per one hour per 1 mol of a titanium atom.

EXAMPLE 5

An autoclave reactor having an inner volume of 0.4 liter equipped with a stirrer was dried under vacuum and purged with argon, then, 198 ml of toluene as a solvent was charged into this, 2 ml of 1-hexeneas an α-olefin was charged, and the reaction vessel was heated up to 60° C. After heating, ethylene was fed while controlling the ethylene pressure at 0.6 MPa, and after the system was stabilized, 0.25 mmol of triisobutylaluminum was charged, subsequently, 0.1 μmol of {chlorobis[1,2-bis(diphenylphosphino)ethane]molybdenum}(μ-dinitrogen) [dichloro(cyclopentadienyl)titanium] was charged, and subsequently, 1.0 μmol of triphenylmethyltetrakis (pentafluorophenyl) borate was charged. Polymerization was conducted for 60 minutes while controlling the temperature at 60° C.

As a result of polymerization, a copolymer of ethylene and 1-hexene having a SCB of 16.4, [η] of 7.5 dl/g, Mw of $4.4 \times 10^5$, Mw/Mn of 2.48 and melting point of 121.0C was produced at a rate of $3.8 \times 10^7$ g per one hour per 1 mol of a titanium atom.

EXAMPLE 6

An autoclave reactor having an inner volume of 0.4 liter equipped with a stirrer was dried under vacuum and purged with argon, then, 185 ml of toluene as a solvent was charged into this, 15 ml of 1-hexene as an α-olefin was charged, and the reaction vessel was heated up to 180° C. After the heating, ethylene was fed while controlling the ethylene pressure at 2.5 MPa, and after the system was stabilized, 0.90 mmol of MMAO was charged, subsequently, a mixture of 0.5 μmol of {chlorobis[1,2-bis(diethylphosphino)ethane]tungsten}(μ-dinitrogen) [dichloro(cyclopentadienyl)titanium] and 0.10 mmol of triisobutylaluminum was charged. Polymerization was conducted for 2 minutes while controlling the temperature at 180° C.

As a result of polymerization, a copolymer of ethylene and 1-hexene having a SCB of 12.6, [1)] of 2.7 dl/g, and melting point of 124.6° C. was produced at a rate of $1.3 \times 10^7$ g per one hour per 1 mol of a titanium atom.

EXAMPLE 7

An autoclave reactor having an inner volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60° C. After the heating, ethylene was fed while controlling the ethylene pressure at 0.6 MPa, and after the system was stabilized, 0.15 mmol of triisobutylaluminum was charged, subsequently, a mixture of 0.05 μmol of {chlorobis[1,2-bis(diethylphosphino)ethane]tungsten}(μ-dinitrogen) [dichloro(cyclopentadienyl)titanium] synthesized in the above-mentioned Example 1(5) and 0.10 mmol of triisobutylaluminum was charged, and subsequently, 1.0 μmol of triphenylmethyltetrakis (pentafluorophenyl)borate was charged. Polymerization was conducted for 60 minutes while controlling the temperature at 60° C.

As a result of polymerization, a copolymer of ethylene and 1-hexene having a SCB of 19.0 and [η] of 3.7 dl/g was produced at a rate of $2.3 \times 10^8$ g per one hour per 1 mol of a titanium atom.

COMPARATIVE EXAMPLE 2

An autoclave reactor having an inner volume of 0.4 liter equipped with a stirrer was dried under vacuum and purged with argon, then, 185 ml of toluene as a solvent was charged into this, 15 ml of 1-hexene as an α-olefin was charged, and the reactor was heated up to 180° C. After the heating, ethylene was fed while controlling the ethylene pressure at 2.5 MPa, and after the system was stabilized, 1.0 mmol of MMAO was charged, and subsequently, 2.5 μmol of (cyclopentadienyl)titanium trichloride was charged. Polymerization was conducted for 2 minutes while controlling the temperature at 180° C.

As a result of polymerization, a copolymer of ethylene and 1-hexene having a Mw of $2.3 \times 10^5$, Mw/Mn of 18.8 and a melting point of 124.3C was produced at a rate of $2.8 \times 10^4$ g per one hour per 1 mol of a titanium atom.

EXAMPLE 8

A glass vessel having an inner volume of 0.1 liter was dried under vacuum and purged with argon, then, 13.8 ml of toluene as a solvent was charged into this, 18.3 ml of styrene was charged, and the reaction vessel was heated up to 50° C. After the heating, 1.0 mmol of triisobutylaluminum was charged, subsequently, 10 μmol of {chlorobis[1,2-bis(diphenylphosphino) ethane]tungsten}(μ-dinitrogen) [trichloro (cyclopentadienyl)niobium](diethylether) synthesized in the above-mentioned Example 1(4) was charged, and subsequently, 30 μm of N,N-dimethylaniliniumtetrakis (pentafluorophenyl) borate was charged. Polymerization was conducted for 60 minutes while controlling the temperature at 50° C.

As a result of polymerization, a styrene polymer having a Mw of $2.1 \times 10^4$ and Mw/Mn of 2.21 was produced at a rate of $1.1 \times 10^6$ g per one hour per 1 mol of a niobium atom.

EXAMPLE 9

An autoclave reactor having an inner volume of 0.4 liter equipped with a stirrer was dried under vacuum and purged with argon, then, 165 ml of toluene as a solvent was charged into this, 35 ml of styrene was charged, and the reaction vessel was heated up to 50° C. After the heating, ethylene was fed while controlling the ethylene pressure at 0.8 MPa, and after the system was stabilized, 2.0 mmol of MMAO was charged, subsequently, 10 μmol of [chlorotetrakis (dimethylphenylphosphine) tungsten) (μ-dinitrogen) [dichloro(cyclopentadienyl) titanium] was charged. Polymerization was conducted for 60 minutes while controlling the temperature at 50° C.

As a result of polymerization, a copolymer of ethylene and styrene having a Mw of $4.3 \times 10^5$, Mw/Mn of 1.96

(converted to polystyrene) and melting point of 108.8° C. was produced at a rate of 4.8×10⁵ g per one hour per 1 mol of a titanium atom.

EXAMPLE 10

An autoclave reactor having an inner volume of 0.4 liter equipped with a stirrer was dried under vacuum and purged with argon, then, 40 ml of toluene as a solvent was charged into this, and the reactor was cooled down to −30° C. After the cooling, 1.0 mmol of triisobutylaluminum was charged, subsequently, 1.0 μmol of [chlorotetrakis (dimethylphenylphosphine)molybdenum](μ-dinitrogen) [dichloro(cyclopentadienyl)titanium] was charged, and subsequently, 6.0 μm of triphenylmethyltetrakis (pentafluorophenyl) borate was charged, and lastly, 80 g of propylene was introduced. After introduction of propylene, the autoclave was heated by polymerization heat, to raise the temperature up to 25° C. After introduction of propylene, polymerization was conducted for 8 minutes.

As a result of polymerization, a propylene polymer having a Mw of 7.4×10⁴, Mw/Mn of 1.98, [mm] of 8.3%, [mr] of 46.3% and [rr] of 45.4% (triad showing stereo regularity) was produced at a rate of 2.0×10⁸ g per one hour per 1 mol of a titanium atom.

EXAMPLE 11

An autoclave reactor having an inner volume of 0.4 liter equipped with a stirrer was dried under vacuum and purged with argon, then, 200 ml of n-hexane as a solvent was charged into this, and the reactor was heated up to 60° C. After temperature raise, ethylene was fed while controlling the ethylene pressure at 0.6 MPa, and after the system was stabilized, 0.50 mmol of tributylaluminum was charged, subsequently, a mixture of 0.01 mmol of {chlorobis[1,2-bis (diethylphosphino)ethane] tungsten}(μ-dinitrogen) [dichloro (pentamethylcyclopentadienyl)titanium] synthesized in the above-mentioned Example 1(6) and 0.01 mmol of triisobutylaluminum was charged, subsequently, 1.0 μmol triphenylmethyltetrakis (pentafluorophenyl) borate was charged. Polymerization was conducted for 60 minutes while controlling the temperature at 60° C.

As a result of polymerization, an ethylene polymer having a Mw of 1.1×10⁶ and Mw/Mn of 2.21 was produced at a rate of 2.3×10⁸ g per one hour per 1 mol of a titanium atom.

EXAMPLE 12

An autoclave reactor having a content volume of 0.4 liter equipped with a stirrer was dried under vacuum and purged with argon, then, 190 ml of n-hexane as a solvent was charged into this, 10 ml of 1-hexene as an α-olefin was charged, and the reaction vessel was heated up to 60° C. After the heating, ethylene was fed while controlling the ethylene pressure at 0.6 MPa, and after the system was stabilized, 0.50 mmol of tributylaluminum was charged, subsequently, a mixture of 0.01 μmol of {chlorobis[1,2-bis (diethylphosphino)ethane] tungsten}(μ-dinitrogen) [dichloro (pentamethylcyclopentadienyl)titanium] synthesized in the above-mentioned Example 1(6) and 0.01 mmol of triisobutylaluminum was charged, subsequently, 1.0 μmol triphenylmethyltetrakis(pentafluorophenyl)borate was charged. Polymerization was conducted for 60 minutes while controlling the temperature at 60° C.

As a result of polymerization, a copolymer of ethylene and 1-hexene having a SCB of 29.2, Mw of 4.2×10⁵ and Mw/Mn of 2.68 was produced at a rate of 8.0×10⁷ g per one hour per 1 mol of a titanium atom.

EXAMPLE 13

An autoclave reactor having a content volume of 0.4 liter equipped with a stirrer was dried under vacuum and purged with argon, then, 190 ml of toluene as a solvent was charged into this, 10 ml of 1-hexene as an α-olefin was charged, and the reaction vessel was heated up to 60° C. After the heating, ethylene was fed while controlling the ethylene pressure at 2.5 MPa, and after the system was stabilized, 0.25 mmol of tributylaluminum was charged, subsequently, 0.025 μmol of {chlorobis[1,2-bis(diethylphosphino)ethane] tungsten)(μ-dinitrogen) [dichloro (pentamethylcyclopentadienyl) titanium] synthesized in the above-mentioned Example 1(6) was charged, and subsequently, 1.2 μmol triphenylmethyltetrakis (pentafluorophenyl)borate was charged. Polymerization was conducted for 60 minutes while controlling the temperature at 60° C.

As a result of polymerization, a copolymer of ethylene and 1-hexene having a SCB of 16.5, Mw of 1.9×10⁶ and Mw/Mn of 2.85 was produced at a rate of 1.9×109 g per one hour per 1 mol of a titanium atom.

EXAMPLE 14

An autoclave reactor having an inner volume of 0.4 liter equipped with a stirrer was dried under vacuum and purged with argon, then, 198 ml of toluene as a solvent was charged into this, 2 ml of 1-hexeneas an α-olefin was charged, and the reaction vessel was heated up to 60° C. After temperature raise, ethylene was fed while controlling the ethylene pressure at 0.6 MPa, and after the system was stabilized, 1.0 mmol of MMAO was charged, and subsequently, 0.02 μmol of {chlorobis[1,2-bis(diethylphosphino)ethane] tungsten} (μ-dinitrogen) [dichloro(indenyl)titanium] synthesized in the above-mentioned Example 1(7) was charged. Polymerization was conducted for 60 minutes while controlling the temperature at 60° C.

As a result of polymerization, a copolymer of ethylene and 1-hexene having a SCB of 15.6, Mw of 6.4×10⁵, and Mw/Mn of 4.26 was produced at a rate of 8.0×10⁷ g per one hour per 1 mol of a titanium atom.

EXAMPLE 15

An autoclave reactor having a content volume of 0.4 liter equipped with a stirrer was dried under vacuum and purged with argon, then, 198 ml of toluene as a solvent was charged into this, 2 ml of 1-hexene as an α-olefin was charged, and the reaction vessel was heated up to 60° C. After the heating, ethylene was fed while controlling the ethylene pressure at 0.6 MPa, and after the system was stabilized, 0.25 mmol of tributylaluminum was charged, subsequently, 0.025 gmol of (chlorobis[1,2-bis(diphenylphosphino)ethane]tungsten)}(μ-dinitrogen) [dichloro (pentamethylcyclopentadienyl) titanium] synthesized in the above-mentioned Example 1(8) was charged, and subsequently, 1.0 μmol triphenylmethyltetrakis (pentafluorophenyl)borate was charged. Polymerization was conducted for 60 minutes while controlling the temperature at 60° C.

As a result of polymerization, a copolymer of ethylene and 1-hexene having a SCB of 16.1, Mw of 9.2×10⁵ and Mw/Mn of 5.99 was produced at a rate of 1.4×10⁸ g per one hour per 1 mol of a titanium atom.

EXAMPLE 16

An autoclave reactor having an inner volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60° C. After temperature raise, ethylene was fed while controlling the ethylene pressure at 0.6 MPa, and after the system was stabilized, 1.0 mmol of MMAO was charged, and subsequently, 0.025 μmol of {chlorobis[1,2-bis(diphenylphosphino)ethane]tungsten}(μ-dinitrogen) [dichloro(pentamethylcyclopentadienyl) titanium] synthesized in the above-mentioned Example 1(8) was charged. Polymerization was conducted for 60 minutes while controlling the temperature at 60° C.

As a result of polymerization, a copolymer of ethylene and 1-hexene having a SCB of 16.1, Mw of $8.0 \times 10^5$, and Mw/Mn of 3.86 was produced at a rate of $1.1 \times 10^8$ g per one hour per 1 mol of a titanium atom.

EXAMPLE 17

An autoclave reactor having an inner volume of 0.4 liter equipped with a stirrer was dried under vacuum and purged with argon, then, 40 ml of toluene as a solvent was charged into this, 80 g of propylene was charged, and the reactor was heated up to 60° C. After the heating and after the system was stabilized, 1.0 mmol of MMAO was charged, and subsequently, 0.10 μmol of {chlorobis[1,2-bis(diphenylphosphino) ethane]tungsten}(μ-dinitrogen) [dichloro(pentamethylcyclopentadienyl) titanium] synthesized in the above-mentioned Example 1(8) was charged. Polymerization was conducted for 60 minutes while controlling the temperature at 60° C.

As a result of polymerization, a propylene polymer having a Mw of $5.6 \times 10^5$, Mw/Mn of 4.00, and [mm] of 13.2%, [mr] of 46.4% and [rr] of 40.4% as triad showing stereo regularity was produced at a rate of $1.6 \times 10^7$ g per one hour per 1 mol of a titanium atom.

EXAMPLE 18

An autoclave reactor having a content volume of 0.4 liter equipped with a stirrer was dried under vacuum and purged with argon, then, 190 ml of toluene as a solvent was charged into this, 10 ml of 1-hexene as an α-olefin was charged, and the reactor was heated up to 60° C. After the heating, ethylene was fed while controlling the ethylene pressure at 0.6 MPa, and after the system was stabilized, 0.25 mmol of trimethylaluminum was charged, subsequently, 0.025 μmol of (bis[1,2-bis(diphenylphosphino)ethane] (isothiocyanide) tungsten} (μ-dinitrogen) [dichloro (cyclopentadienyl) titanium] (3.dichloromethane) synthesized in the above-mentioned Example 1(9) was charged, and subsequently, 1.0 μmol triphenylmethyltetrakis (pentafluorophenyl)borate was charged. Polymerization was conducted for 60 minutes while controlling the temperature at 60° C.

As a result of polymerization, a copolymer of ethylene and 1-hexene having a SCB of 26.4, Mw of $3.4 \times 10^5$ and Mw/Mn of 2.23 was produced at a rate of $2.9 \times 10^8$ g per one hour per 1 mol of a titanium atom.

EXAMPLE 19

An autoclave reactor having an inner volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60C. After temperature raise, ethylene was fed while controlling the ethylene pressure at 0.6 MPa, and after the system was stabilized, 1.0 mmol of MMAO was charged, and subsequently, 0.0125 μmol of {bis[1,2-bis(diphenylphosphino)ethane] (isothiocyanide) tungsten} (1-dinitrogen) [dichloro (cyclopentadienyl) titanium] (3.dichloromethane) synthesized in the above-mentioned Example 1(9) was charged. Polymerization was conducted for 60 minutes while controlling the temperature at 60° C.

As a result of polymerization, a copolymer of ethylene and 1-hexene having a SCB of 16.5, Mw of $7.9 \times 10^5$, and Mw/Mn of 2.32 was produced at a rate of $3.6 \times 108$ g per one hour per 1 mol of a titanium atom.

EXAMPLE 20

An autoclave reactor having a content volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60°C. After the heating, ethylene was fed while controlling the ethylene pressure at 0.6 MPa, and after the system was stabilized, 0.25 mmol of tri-n-octylaluminum was charged, subsequently, 0.025 μmol of {chlorobis[1,2-bis(diphenylphosphino)ethane]tungusten} (μ-dinitrogen) [dichloro(methylcyclopentadienyl) titanium] synthesized in the above-mentioned Example 1(10) was charged, and subsequently, 1.0 μmol triphenylmethyltetrakis (pentafluorophenyl)borate was charged. Polymerization was conducted for 60 minutes while controlling the temperature at 60° C.

As a result of polymerization, a copolymer of ethylene and 1-hexene having a SCB of 18.1, Mw of $1.3 \times 106$ and Mw/Mn of 3.11 was produced at a rate of $4.3 \times 10^8$ g per one hour per 1 mol of a titanium atom.

EXAMPLE 21

An autoclave reactor having an inner volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60° C. After temperature raise, ethylene was fed while controlling the ethylene pressure at 0.6 MPa, and after the system was stabilized, 1.0 mmol of MMAO was charged, and subsequently, 0.025 gmol of {chlorobis[1,2-bis(diphenylphosphino) ethane] tungusten} (μ-dinitrogen) [dichloro(methylcyclopentadienyl) titanium] synthesized in the above-mentioned Example 1(10) was charged. Polymerization was conducted for 60 minutes while controlling the temperature at 60° C.

As a result of polymerization, a copolymer of ethylene and 1-hexene having a SCB of 16.9, Mw of $9.0 \times 1O$, and Mw/Mn of 3.40 was produced at a rate of $2.2 \times 10^8$ g per one hour per 1 mol of a titanium atom.

EXAMPLE 22

An autoclave reactor having an inner volume of 0.4 liter equipped with a stirrer was dried under vacuum and purged with argon, then, 40 ml of toluene as a solvent was charged into this, 80 g of propylene was charged, and the reactor was heated up to 60° C. After the heating and after the system was stabilized, 1.0 mmol of MMAO was charged, and subsequently, 0.10 μmol of {chlorobis[1,2-bis (diphenylphosphino) ethane] tungusten}(μ-dinitrogen) [dichloro(methylcyclopentadienyl) titanium] synthesized in the above-mentioned Example 1(10) was charged. Polymerization was conducted for 60 minutes while controlling the temperature at 60° C.

As a result of polymerization, a propylene polymer having a Mw of $1.3 \times 10^5$, Mw/Mn of 1.80, and [mm] of 10.4%,

[mr] of 44.2% and [rr] of 45.4% as triad showing stereo regularity was produced at a rate of 4.4×10 g per one hour per 1 mol of a titanium atom.

EXAMPLE 23

An autoclave reactor having a content volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60° C. After the heating, ethylene was fed while controlling the ethylene pressure at 0.6 MPa, and after the system was stabilized, 0.25 mmol of triisobutylaluminum was charged, subsequently, 0.025 μmol of {chlorobis[1,2-bis(diethylphosphino)ethane]tungsten}(μ-dinitrogen) [dichloro(methylcyclopentadienyl)titanium] synthesized in the above-mentioned Example 1(11) was charged, and subsequently, 1.0 μmol triphenylmethyltetrakis (pentafluorophenyl)borate was charged. Polymerization was conducted for 60 minutes while controlling the temperature at 60° C.

As a result of polymerization, a copolymer of ethylene and 1-hexene having a SCB of 16.3, Mw of $2.8 \times 10^5$ and Mw/Mn of 1.95 was produced at a rate of $2.5 \times 10^8$ g per one hour per 1 mol of a titanium atom.

EXAMPLE 24

An autoclave reactor having an inner volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60° C. After temperature raise, ethylene was fed while controlling the ethylene pressure at 0.6 MPa, and after the system was stabilized, 1.0 mmol of MMAO was charged, and subsequently, 0.025 μmol of {chlorobis[1,2-bis(diethylphosphino)ethane]tungsten}(μ-dinitrogen) [dichloro(methylcyclopentadienyl)titanium] synthesized in the above-mentioned Example 1(11) was charged. Polymerization was conducted for 60 minutes while controlling the temperature at 60° C.

As a result of polymerization, a copolymer of ethylene and 1-hexene having a SCB of 16.7, Mw of $4.8 \times 10^5$, and Mw/Mn of 2.94 was produced at a rate of $1.5 \times 10^8$ g per one hour per 1 mol of a titanium atom.

EXAMPLE 25

An autoclave reactor having an inner volume of 0.4 liter equipped with a stirrer was dried under vacuum and purged with argon, then, 170 ml of toluene as a solvent was charged into this, 30 ml of 1-hexene as an α-olefin was charged, and the reactor was heated up to 180° C. After temperature raise, ethylene was fed while controlling the ethylene pressure at 2.5 MPa, and after the system was stabilized, 1.0 mmol of MMAO was charged, and subsequently, 0.25 μmol of {chlorobis[1,2-bis(diethylphosphino)ethane]tungsten}(μ-dinitrogen) [dichloro(methylcyclopentadienyl)titanium] synthesized in the above-mentioned Example 1(11) was charged. Polymerization was conducted for 2 minutes while controlling the temperature at 180° C.

As a result of polymerization, a copolymer of ethylene and 1-hexene having a SCB of 13.1, Mw of $6.8 \times 10^4$, and Mw/Mn of 2.07 was produced at a rate of $6.4 \times 10^8$ g per one hour per 1 mol of a titanium atom.

EXAMPLE 26

An autoclave reactor having a content volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60° C. After the heating, ethylene was fed while controlling the ethylene pressure at 0.6 MPa, and after the system was stabilized, 0.35 mmol of triisobutylaluminum was charged, subsequently, 1.0 μmol of (chlorobis[1,2-bis(diphenylphosphino)ethane]tungsten}(μ-dinitrogen)[trichloro(cyclopentadienyl)niobium] (diethylether) synthesized in the above-mentioned Example 1(4) was charged, and subsequently, 6.0 μmol triphenylmethyltetrakis (pentafluorophenyl)borate was charged. Polymerization was conducted for 60 minutes while controlling the temperature at 60° C.

As a result of polymerization, a copolymer of ethylene and 1-hexene having a SCB of 10.1, Mw of $6.3 \times 10^4$ and Mw/Mn of 1.78 was produced at a rate of $4.9 \times 10^6$ g per one hour per 1 mol of a niobium atom.

EXAMPLE 27

[chlorotetrakis(dimethylphenylphosphine)tungsten](μ-dinitrogen)[trichloro(pentamethylcyclopentadienyl)niobium](toluene) shown below as a transition metal compound was used.

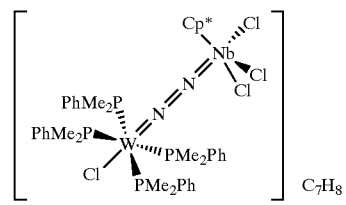

An autoclave reactor having a content volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60° C. After the heating, ethylene was fed while controlling the ethylene pressure at 0.6 MPa, and after the system was stabilized, 0.45 mmol of triisobutylaluminum was charged, subsequently, 2.0 μmol of [chlorotetrakis(dimethylphenylphosphine)tungsten](μ-dinitrogen) [trichloro(pentamethylcyclopentadienyl)niobium] (toluene) synthesized in the above-mentioned Example 1(12) was charged, and subsequently, 3.0 μmol triphenylmethyltetrakis (pentafluorophenyl)borate was charged. Polymerization was conducted for 60 minutes while controlling the temperature at 60° C. As a result of polymerization, a copolymer of ethylene and 1-hexene having a SCB of 8.3, Mw of $8.9 \times 10^4$ and Mw/Mn of 2.21 was produced at a rate of $10 \times 10^6$ g per one hour per 1 mol of a niobium atom.

EXAMPLE 28

[chlorotetrakis(dimethylphenylphosphine) tungsten](μ-dinitrogen)[trichloro(cyclopentadienyl) tantalum] (dichloromethane) shown below as a transition metal compound was used.

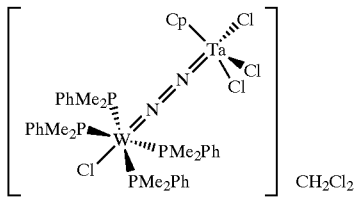

An autoclave reactor having a content volume of 0.4 liter equipped with a stirrer was dried under vacuum and purged with argon, then, 198 ml of toluene as a solvent was charged into this, 2 ml of 1-hexene as an α-olefin was charged, and the reactor was heated up to 60° C. After the heating, ethylene was fed while controlling the ethylene pressure at 0.6 MPa, and after the system was stabilized, 0.45 mmol of triisobutylaluminum was charged, subsequently, 2.0 μmol of [chlorotetrakis(dimethylphenylphosphine)tungsten](μ-dinitrogen)[trichloro(cyclopentadienyl)tantalum] (dichlorom ethane) synthesized in the above-mentioned Example 1(13) was charged, and subsequently, 3.0 μmol triphenylmethyltetrakis (pentafluorophenyl)borate was charged. Polymerization was conducted for 60 minutes while controlling the temperature at 60 C. As a result of polymerization, a copolymer of ethylene and 1-hexene having a SCB of 7.5, Mw of $6.4 \times 10^4$ and Mw/Mn of 1.74 was produced at a rate of $6.0 \times 10^5$ g per one hour per 1 mol of a tantalum atom.

As described in detail above, the present invention provides a catalyst component for addition polymerization composed of a transition metal compound which can manifest high activity, a catalyst for addition polymerization prepared by using this catalyst component for addition polymerization, and an efficient process for producing an addition polymer, using this catalyst for addition polymerization.

What is claimed is:

1. A catalyst for addition polymerization obtained by a process comprising bringing a transition metal compound (A) represented by the general formula (1):

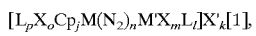

wherein M and M' each independently represents a transition metal atom of Group 3 to 10 in the Periodic Table of the Elements; X each independently represents a hydrogen atom, halogen atom, alkyl group, aralkyl group, aryl group, substituted silyl group substituted with a hydrocarbon group, alkoxy group, aralkyloxy group, aryloxy group, di-substituted amino group substituted with two hydrocarbon groups, azido group, cyano group or isothiocyanate group; Cp is a group having a cyclopentadiene anion skeleton; L represents a group which bonds to M or M' by lone pair of electrons or a πelectron; X' represents a counter anion; k, l, m, o and p each independently represent an integer of 0 to 5; j represents an integer of 0 to 2; n+o+p+j≦6; n represents an integer of 1 to 3; and n+l+m≦6, into contact with an organoaluminum compound selected from the group consisting of the following (B 1), and at least one aluminoxane selected from the group consisting of the following (B2) and (B3) and/or the following (C):

(B1) organoaluminum compounds of the general formula $E^1{}_a AlZ_{3-a}$, (B2) cyclic aluminoxanes having a structure of the general formula $\{-Al(E^2)-O-\}_b$, (B3) linear aluminoxanes having a structure of the general formula $E^3\{-Al(E^3)-O-\}_c AlE^3{}_2$, (wherein, each of $E^1$, $E^2$ and $E^3$ represents a hydrocarbon group; all $E^1$s, all $E^2$s or all $E^3$s maybe the same or different; Z represents a hydrogen atom or halogen atom; all Zs may be the same or different; a represents a number satisfying 0<a≦3; b represents an integer of 2 or more; and c represents an integer of 1 or more,), and (C) one or more boron compounds selected from the following (Cl) to (C3):

(C1) boron compounds represented by the general formula $BQ_1Q^2Q^3$, (C2) boron compounds represented by the general formula $G^+(BQ^1Q^2Q^3Q^4)-$, and (C3) boron compounds represented by the general formula $(L-H)^+(BQ^1Q^2Q^3Q^4)$, wherein, B represents boron in trivalent state; $Q^1$ to $Q^4$ represent a halogen atom, hydrocarbon group, halogenated hydrocarbon group, substituted silyl group, alkoxy group or di-substituted amino group; they may be the same or different; $G^+$represents an inorganic or organic cation; L represents a neutral Lewis base; and $(L-H)^+$ represents a Bønsted acid.

2. The catalyst according to claim 1, wherein M represents a transition metal atom of Group 3 to 5.

3. The catalyst according to claim 1, wherein M' represents a transition metal atom of Group 6 to 10.

4. The catalyst according to claim 1, wherein M represents a transition metal atom of Group 3 to 5 and M' represents a transition metal atom of Group 6 to 10.

5. The catalyst according to claim 1, wherein j is 0 or 1.

6. The catalyst according to claim 1, wherein j is 1, and n+m+1 is 6.

7. A process for producing an addition polymer which comprises polymerizing an addition polymerizable monomer with the catalyst defined in claim 1.

8. A process for producing an addition polymer which comprises polymerizing an addition polymerizable monomer with the catalyst defined in claim 2.

9. A process for producing an addition polymer which comprises polymerizing an addition polymerizable monomer with the catalyst defined in claim 3.

10. A process for producing an addition polymer which comprises polymerizing an addition polymerizable monomer with the catalyst defined in claim 4.

11. A process for producing an addition polymer which comprises polymerizing an addition polymerizable monomer with the catalyst defined in claim 5.

12. A process for producing an addition polymer which comprises polymerizing an addition polymerizable monomer with the catalyst defined in claim 6.

13. A transition metal compound represented by the general formula [1]:

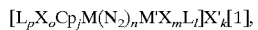

wherein M and M' each independently represent a transition metal atom of Group 3 to 10 in the Periodic Table of the Elements; X each independently represents a hydrogen atom, halogen atom, alkyl group, aralkyl group, aryl group, substituted silyl group substituted with a hydrocarbon group, alkoxy group, aralkyloxy group, aryloxy group, di-substituted amino group substituted with two hydrocarbon groups, azido group, cyano group or isothiocyanate group; Cp is a group having a cyclopentadiene anion skeleton; L represents a group which bonds to M or M' by lone pair of electrons or a π electron; X' represents a counter anion; k, l, m, o and p each independently represent an integer of 0 to 5; j represents 0 or 1; n+o+p+j≦6; n represents an integer of 1 to 3; and n+l+m≦6.

14. The transition metal compound according to claim 13, wherein M represents a transition metal atom of Group 3 to 5.

15. The transition metal compound according to claim 13, wherein M' represents a transition metal atom of Group 6 to 10.

16. The transition metal compound according to claim 13, wherein M represents a transition metal atom of Group 3 to 5 and M' represents a transition metal atom of Group 6 to 10.

17. The transition metal compound according to claim 13, wherein j is 1, and n+m+1 is 6.

18. The transition metal compound according to claim 13, wherein the component is a member selected from the group consisting of [chlorotetrakis(dimethylphenylphosphine)tungsten] (μ-dinitrogen) [dichloro(cyclopentadienyl)titanium], {chlorobis[1,2-bis(diphenylphosphino)ethane]tungsten}(μ-dinitrogen) [dichloro(cyclopentadienyl)titanium](diethyl ether)(dichloromethane), {chlorobis[1,2-bis(diphenylphosphino)ethane] molybdenum}(μ-dinitrogen) [dichloro (cyclopentadienyl)titanium], {chlorobis[1,2-bis(diphenylphosphino)ethane]tungsten}(μ-dinitrogen)[trichloro(cyclopentadienyl)niobium] (diethylether), (chlorobis[1,2-bis(diethylphosphino) ethane] tungsten)(μ-dinitrogen) [dichloro(cyclopentadienyl)titanium], (chlorobis[1,2-bis(diethylphosphino)ethane] tungsten) (μ-dinitrogen) [dichloro (pentamethylcyclopentadienyl)titanium], {chlorobis[1,2-bis(diethylphosphino)ethane] tungsten}(μ-dinitrogen) [dichloro(indenyl)titanium], (chlorobis[1,2-bis(diphenylphosphino)ethane]tungsten)(μ-dinitrogen) [dichloro(pentamethylcyclopentadienyl) titanium], {bis[1,2-bis(diphenylphosphino)ethane] (isothiocyanide)tungusten} (μ-dinitrogen) [dichloro (cyclopentadienyl)titanium](3-dichloromethane), (chlorobis[1,2-bis(diphenylphosphino) ethane]tungusten)(μ-dinitrogen) [dichloro (methylcyclopentadienyl) titanium] and (chlorobis[1,2-bis(diethylphosphino)ethane]tungusten)(μ-dinitrogen) [dichloro(methylcyclopentadienyl)titanium].

* * * * *